(12) United States Patent
Nottrott et al.

(10) Patent No.: US 12,216,105 B2
(45) Date of Patent: Feb. 4, 2025

(54) LOCALIZATION ANALYTICS ALGORITHMS AND METHODS

(71) Applicant: SeekOps Inc., Austin, TX (US)

(72) Inventors: Anders Andelman Nottrott, Santa Barbara, CA (US); Brendan James Smith, Lakeway, TX (US); Andrew David Aubrey, Austin, TX (US)

(73) Assignee: SeekOps Inc., Austin, TX (US)

( * ) Notice: Subject to any disclaimer, the term of this patent is extended or adjusted under 35 U.S.C. 154(b) by 865 days.

(21) Appl. No.: 17/251,089

(22) PCT Filed: Jun. 19, 2019

(86) PCT No.: PCT/US2019/038015
§ 371 (c)(1),
(2) Date: Dec. 10, 2020

(87) PCT Pub. No.: WO2019/246283
PCT Pub. Date: Dec. 26, 2019

(65) Prior Publication Data
US 2021/0247369 A1 Aug. 12, 2021

Related U.S. Application Data

(60) Provisional application No. 62/687,152, filed on Jun. 19, 2018.

(51) Int. Cl.
*G01N 33/00* (2006.01)
*B64U 10/14* (2023.01)
(Continued)

(52) U.S. Cl.
CPC ..... *G01N 33/0047* (2013.01); *G01N 33/0067* (2013.01); *B64U 10/14* (2023.01);
(Continued)

(58) Field of Classification Search
CPC .......... G01N 33/0047; G01N 33/0036; G01N 33/0027; G01N 33/00097; G01N 33/0004;
(Continued)

(56) References Cited

U.S. PATENT DOCUMENTS 3,780,566 A 12/1973 Smith et al.
4,135,092 A 1/1979 Milly
(Continued)

FOREIGN PATENT DOCUMENTS

AU 3401499 A 11/1999
CN 101470072 A 7/2009
(Continued)

OTHER PUBLICATIONS

U.S. Appl. No. 62/687,147, filed Jun. 19, 2018, Brendan James Smith.
(Continued)

*Primary Examiner* — Mohamed Charioui
(74) *Attorney, Agent, or Firm* — Command IP LLP; Michael Zarrabian

(57) ABSTRACT

Systems, devices, and methods for receiving, by a ground control station (GCS) having a processor with addressable memory, a plurality of point source gas concentration measurements; receiving, by the GCS, a meteorological data corresponding to each point source concentration gas measurement; determining, by the GCS, if each point source gas concentration measurement is an elevated ambient gas concentration; generating, by the GCS, a back trajectory for each elevated ambient gas concentration; storing, by the GCS, the position of each generated back trajectory in a grid; determining, by the GCS, a probability of a gas source location corresponding to the stored positions in the grid;
(Continued)

and generating, by the GCS, an overlay showing the probability of the gas source location.

20 Claims, 19 Drawing Sheets

(51) Int. Cl.
  *B64U 101/26* (2023.01)
  *B64U 101/30* (2023.01)
  *B64U 101/35* (2023.01)
(52) U.S. Cl.
  CPC ...... *B64U 2101/26* (2023.01); *B64U 2101/30* (2023.01); *B64U 2101/35* (2023.01); *B64U 2201/104* (2023.01); *B64U 2201/20* (2023.01)
(58) Field of Classification Search
  CPC ............... G01N 33/00; G01N 33/0067; G01N 33/0062; G01N 33/0097; B64C 39/024; B64U 2101/35; B64U 2101/00; B64U 2201/104; B64U 2201/10; B64U 2201/20; B64U 2201/00
  See application file for complete search history.

(56) References Cited

U.S. PATENT DOCUMENTS

| | | | |
|---|---|---|---|
| 4,233,564 A | 11/1980 | Kerbel | |
| 4,507,558 A | 3/1985 | Bonne | |
| 4,988,833 A | 1/1991 | Lai | |
| 5,047,639 A | 9/1991 | Wong | |
| 5,075,619 A | 12/1991 | Said | |
| 5,173,749 A | 12/1992 | Tell et al. | |
| 5,291,265 A | 3/1994 | Kebabian | |
| 5,317,156 A | 5/1994 | Cooper et al. | |
| 5,767,780 A | 6/1998 | Smith et al. | |
| 5,822,058 A | 10/1998 | Adler-Golden et al. | |
| 6,064,488 A | 5/2000 | Brand et al. | |
| 6,295,859 B1 | 10/2001 | Hayden et al. | |
| 6,356,350 B1 | 3/2002 | Silver et al. | |
| 6,509,566 B1 | 1/2003 | Wamsley et al. | |
| 6,549,630 B1 | 4/2003 | Bobisuthi | |
| 7,162,933 B2 | 1/2007 | Thompson et al. | |
| 7,800,751 B1 | 9/2010 | Silver et al. | |
| 7,833,480 B2 | 11/2010 | Blazewicz et al. | |
| 8,060,270 B2 | 11/2011 | Vian et al. | |
| 8,294,899 B2 | 10/2012 | Wong | |
| 8,451,120 B2 | 5/2013 | Johnson, Jr. et al. | |
| 8,730,461 B2 | 5/2014 | Andreussi | |
| 9,183,371 B2 | 11/2015 | Narendra et al. | |
| 9,183,731 B1 | 11/2015 | Bokhary | |
| 9,235,974 B2 | 1/2016 | Johnson, Jr. et al. | |
| 9,250,175 B1 | 2/2016 | McManus | |
| 9,494,511 B2 | 11/2016 | Wilkins | |
| 9,599,529 B1 | 3/2017 | Steele et al. | |
| 9,599,597 B1* | 3/2017 | Steele ..................... G01M 3/04 | |
| 10,023,311 B2 | 7/2018 | Lai et al. | |
| 10,023,323 B1 | 7/2018 | Roberts et al. | |
| 10,031,040 B1 | 7/2018 | Smith et al. | |
| 10,126,200 B1 | 11/2018 | Steele et al. | |
| 10,268,198 B2 | 4/2019 | Mantripragada et al. | |
| 10,325,485 B1 | 6/2019 | Schuster | |
| 10,365,646 B1 | 7/2019 | Farnsworth et al. | |
| 10,429,546 B1 | 10/2019 | Ulmer | |
| 10,677,771 B2 | 6/2020 | Dittberner et al. | |
| 10,753,864 B2 | 8/2020 | Kasten et al. | |
| 10,816,458 B2 | 10/2020 | Kasten et al. | |
| 10,830,034 B2 | 11/2020 | Cooley et al. | |
| 10,962,437 B1 | 3/2021 | Nottrott et al. | |
| 11,105,784 B2 | 8/2021 | Kukreja et al. | |
| 11,112,308 B2 | 9/2021 | Kreitinger et al. | |
| 11,275,068 B2 | 3/2022 | Willett | |
| 11,299,268 B2 | 4/2022 | Christensen et al. | |
| 11,519,855 B2 | 12/2022 | Black et al. | |
| 11,557,212 B2 | 1/2023 | Hong | |
| 11,614,430 B2 | 3/2023 | Buckingham et al. | |
| 11,619,562 B2 | 4/2023 | Leen et al. | |
| 11,710,411 B2 | 7/2023 | Van Meeteren et al. | |
| 11,748,866 B2 | 9/2023 | Vargas | |
| 2002/0005955 A1 | 1/2002 | Kramer et al. | |
| 2003/0160174 A1 | 8/2003 | Grant et al. | |
| 2003/0189711 A1 | 10/2003 | Orr et al. | |
| 2003/0230716 A1 | 12/2003 | Russell et al. | |
| 2004/0012787 A1 | 1/2004 | Galle et al. | |
| 2004/0017762 A1 | 1/2004 | Sogawa et al. | |
| 2004/0212804 A1 | 10/2004 | Neff et al. | |
| 2006/0015290 A1 | 1/2006 | Warburton et al. | |
| 2006/0044562 A1 | 3/2006 | Hagene et al. | |
| 2006/0232772 A1 | 10/2006 | Silver | |
| 2006/0234621 A1 | 10/2006 | Desrochers et al. | |
| 2007/0137318 A1 | 6/2007 | Desrochers et al. | |
| 2008/0169934 A1 | 7/2008 | Lang et al. | |
| 2008/0243372 A1 | 10/2008 | Bodin et al. | |
| 2009/0201507 A1 | 8/2009 | Kluczynski et al. | |
| 2009/0263286 A1 | 10/2009 | Isomura et al. | |
| 2009/0326792 A1 | 12/2009 | McGrath | |
| 2010/0004798 A1 | 1/2010 | Bodin et al. | |
| 2010/0131207 A1 | 5/2010 | Lippert et al. | |
| 2010/0140478 A1 | 6/2010 | Wilson et al. | |
| 2010/0147081 A1 | 6/2010 | Thomas | |
| 2011/0035149 A1 | 2/2011 | McAndrew et al. | |
| 2011/0074476 A1 | 3/2011 | Heer et al. | |
| 2011/0150035 A1 | 6/2011 | Hanson et al. | |
| 2011/0164251 A1 | 7/2011 | Richter | |
| 2011/0213554 A1 | 9/2011 | Archibald et al. | |
| 2011/0242659 A1 | 10/2011 | Eckles et al. | |
| 2011/0257944 A1 | 10/2011 | Du et al. | |
| 2012/0120397 A1 | 5/2012 | Furtaw et al. | |
| 2013/0044314 A1 | 2/2013 | Koulikov et al. | |
| 2013/0076900 A1 | 3/2013 | Mrozek et al. | |
| 2013/0208262 A1 | 8/2013 | Andreussi | |
| 2014/0172323 A1 | 6/2014 | Marino | |
| 2014/0204382 A1 | 7/2014 | Christensen | |
| 2014/0236390 A1 | 11/2014 | Mohamadi | |
| 2014/0336957 A1 | 11/2014 | Hanson et al. | |
| 2015/0072633 A1 | 3/2015 | Massarella et al. | |
| 2015/0145954 A1 | 5/2015 | Pulleti et al. | |
| 2015/0226575 A1 | 8/2015 | Rambo | |
| 2015/0275114 A1 | 10/2015 | Tumiatti et al. | |
| 2015/0295543 A1 | 10/2015 | Brown et al. | |
| 2015/0316473 A1 | 11/2015 | Kester et al. | |
| 2015/0323449 A1 | 11/2015 | Jones et al. | |
| 2015/0336667 A1 | 11/2015 | Srivastava et al. | |
| 2016/0018373 A1 | 1/2016 | Pagé et al. | |
| 2016/0070265 A1 | 3/2016 | Liu et al. | |
| 2016/0104250 A1 | 4/2016 | Allen et al. | |
| 2016/0146696 A1 | 5/2016 | Steele et al. | |
| 2016/0161456 A1* | 6/2016 | Risk ......................... G01P 5/06 |  |
| | | | 702/24 |
| 2016/0202225 A1 | 7/2016 | Feng et al. | |
| 2016/0214715 A1 | 7/2016 | Meffert | |
| 2016/0307447 A1 | 10/2016 | Johnson et al. | |
| 2016/0357192 A1 | 12/2016 | McGrew et al. | |
| 2017/0003684 A1 | 1/2017 | Knudsen et al. | |
| 2017/0057081 A1 | 3/2017 | Krohne et al. | |
| 2017/0089829 A1 | 3/2017 | Bartholomew et al. | |
| 2017/0093122 A1 | 3/2017 | Bean et al. | |
| 2017/0097274 A1* | 4/2017 | Thorpe ................... G01C 15/00 | |
| 2017/0115218 A1 | 4/2017 | Huang et al. | |
| 2017/0134497 A1 | 5/2017 | Harter et al. | |
| 2017/0158353 A1 | 6/2017 | Schmick | |
| 2017/0199647 A1 | 7/2017 | Richman et al. | |
| 2017/0206648 A1 | 7/2017 | Marra et al. | |
| 2017/0235018 A1 | 8/2017 | Foster et al. | |
| 2017/0259920 A1 | 9/2017 | Lai et al. | |
| 2017/0307519 A1 | 10/2017 | Black et al. | |
| 2017/0336281 A1 | 11/2017 | Waxman et al. | |
| 2017/0339820 A1 | 11/2017 | Foster et al. | |
| 2018/0023974 A1 | 1/2018 | Otani et al. | |
| 2018/0024091 A1 | 1/2018 | Wang et al. | |
| 2018/0045561 A1 | 2/2018 | Leen et al. | |
| 2018/0045596 A1* | 2/2018 | Prasad ..................... G01M 3/22 | |
| 2018/0050798 A1 | 2/2018 | Kapuria | |

(56) References Cited

U.S. PATENT DOCUMENTS

| | | |
|---|---|---|
| 2018/0059003 A1 | 3/2018 | Jourdainne et al. |
| 2018/0067066 A1 | 3/2018 | Giedd et al. |
| 2018/0109767 A1 | 4/2018 | Li et al. |
| 2018/0122246 A1 | 5/2018 | Clark |
| 2018/0127093 A1 | 5/2018 | Christensen et al. |
| 2018/0188129 A1 | 7/2018 | Choudhury et al. |
| 2018/0259955 A1 | 9/2018 | Noto |
| 2018/0266241 A1 | 9/2018 | Ferguson et al. |
| 2018/0266946 A1 | 9/2018 | Kotidis et al. |
| 2018/0209902 A1 | 10/2018 | Myshak et al. |
| 2018/0284088 A1 | 10/2018 | Verbeck, IV |
| 2018/0292374 A1* | 10/2018 | Dittberner ............ G08G 5/0086 |
| 2018/0321692 A1 | 11/2018 | Castillo-Effen et al. |
| 2018/0322699 A1 | 11/2018 | Gray et al. |
| 2019/0011920 A1 | 1/2019 | Heinonen et al. |
| 2019/0011935 A1 | 1/2019 | Ham et al. |
| 2019/0025199 A1 | 1/2019 | Koulikov |
| 2019/0033194 A1 | 1/2019 | DeFreez et al. |
| 2019/0049364 A1 | 2/2019 | Rubin |
| 2019/0077506 A1 | 3/2019 | Shaw et al. |
| 2019/0086202 A1 | 3/2019 | Guan et al. |
| 2019/0095687 A1 | 3/2019 | Shaw et al. |
| 2019/0154874 A1 | 5/2019 | Shams et al. |
| 2019/0178743 A1 | 6/2019 | McNeil |
| 2019/0195789 A1 | 6/2019 | Pan et al. |
| 2019/0204189 A1 | 7/2019 | Mohr, Jr. et al. |
| 2019/0212419 A1 | 7/2019 | Jeong et al. |
| 2019/0220019 A1 | 7/2019 | Tan et al. |
| 2019/0228573 A1 | 7/2019 | Sen et al. |
| 2019/0234868 A1 | 8/2019 | Tanomura et al. |
| 2019/0331652 A1 | 10/2019 | Ba et al. |
| 2020/0050189 A1 | 2/2020 | Gu et al. |
| 2020/0065433 A1 | 2/2020 | Duff et al. |
| 2020/0109976 A1 | 4/2020 | Ajay et al. |
| 2020/0135036 A1 | 4/2020 | Campbell |
| 2020/0182779 A1 | 6/2020 | Kasten et al. |
| 2020/0249092 A1 | 8/2020 | Podmore et al. |
| 2020/0373172 A1 | 11/2020 | Suzuki |
| 2020/0400635 A1 | 12/2020 | Potyrailo et al. |
| 2021/0017926 A1 | 1/2021 | Alkadi et al. |
| 2021/0037197 A1 | 2/2021 | Kester et al. |
| 2021/0055180 A1 | 2/2021 | Thorpe et al. |
| 2021/0109074 A1 | 4/2021 | Smith et al. |
| 2021/0140934 A1 | 5/2021 | Smith et al. |
| 2021/0190745 A1 | 6/2021 | Buckingham et al. |
| 2021/0190918 A1 | 6/2021 | Li et al. |
| 2021/0199565 A1 | 7/2021 | John et al. |
| 2021/0247369 A1 | 8/2021 | Nottrott et al. |
| 2021/0255158 A1 | 8/2021 | Smith et al. |
| 2021/0300591 A1 | 9/2021 | Tian |
| 2021/0321174 A1 | 10/2021 | Sun et al. |
| 2021/0364427 A1 | 11/2021 | Smith et al. |
| 2021/0382475 A1 | 12/2021 | Smith et al. |
| 2022/0082495 A1 | 3/2022 | Kreitinger et al. |
| 2022/0113290 A1 | 4/2022 | Smith et al. |
| 2022/0170810 A1 | 6/2022 | Miller et al. |
| 2022/0268952 A1 | 8/2022 | Liang et al. |
| 2022/0341806 A1 | 10/2022 | Miller et al. |
| 2022/0357231 A1 | 11/2022 | Nahata et al. |
| 2023/0194487 A1 | 6/2023 | Buckingham et al. |
| 2023/0213413 A1 | 7/2023 | Mohr, Jr. et al. |
| 2023/0274651 A1 | 8/2023 | McGuire et al. |
| 2023/0392498 A1 | 12/2023 | Srivastav et al. |

FOREIGN PATENT DOCUMENTS

| | | |
|---|---|---|
| CN | 104458588 A | 3/2015 |
| CN | 205749271 U | 11/2016 |
| CN | 106568516 A | 4/2017 |
| CN | 106769977 A | 5/2017 |
| CN | 107703075 A | 2/2018 |
| CN | 109780452 A | 5/2019 |
| CN | 211508182 U | 9/2020 |
| CN | 112213443 A | 1/2021 |
| DE | 29601472 U1 | 5/1996 |
| DE | 69333010 | 4/2004 |
| DE | 102014013822 A1 | 3/2016 |
| EP | 0450809 A2 | 10/1991 |
| EP | 1371962 B1 | 7/2011 |
| EP | 3339855 A1 | 6/2018 |
| FR | 3047073 A1 | 7/2017 |
| FR | 3047073 B1 | 8/2019 |
| GB | 2538563 A | 11/2016 |
| JP | H08247939 A | 9/1996 |
| JP | 200975823 A | 4/2009 |
| KR | 20170062813 A | 6/2017 |
| KR | 101770254 B1 | 8/2017 |
| TW | 522226 B | 3/2003 |
| WO | 1999054700 A2 | 10/1999 |
| WO | 02066950 A1 | 8/2002 |
| WO | 2008021311 A2 | 2/2008 |
| WO | 2015073687 A1 | 5/2015 |
| WO | 2016045791 A1 | 3/2016 |
| WO | 2016162673 A1 | 10/2016 |
| WO | 2017069979 A1 | 4/2017 |
| WO | 2018121478 A1 | 7/2018 |
| WO | 2018227153 A1 | 12/2018 |
| WO | 2019246280 A1 | 12/2019 |
| WO | 2020007684 A1 | 1/2020 |
| WO | 2020028353 A1 | 2/2020 |
| WO | 2020086499 A1 | 4/2020 |
| WO | 2020206006 A1 | 10/2020 |
| WO | 2020206008 A1 | 10/2020 |
| WO | 2020206020 A1 | 10/2020 |
| WO | 2021055902 A1 | 3/2021 |
| WO | 2021158916 A1 | 8/2021 |
| WO | 2022093864 A1 | 5/2022 |
| WO | 2022211837 A1 | 10/2022 |

OTHER PUBLICATIONS

"Safesite Multi-Threat Detection System", Jul. 11, 2012 (Jul. 11, 2012), pp. 1-6, XP055245980.
International Search Report and Written Opinion for PCT/US19/38011 mailed Sep. 9, 2019.
International Search Report and Written Opinion for PCT/US19/44119, mailed Oct. 17, 2019.
International Search Report and Written Opinion for PCT/US20/26228 mailed Jul. 1, 2020.
International Search Report and Written Opinion for PCT/US20/26232 mailed Jun. 26, 2020.
International Search Report and Written Opinion for PCT/US20/26246 mailed Jun. 29, 2020.
International Search Report and Written Opinion for PCT/US20/51696, mailed Feb. 3, 2021.
International Search Report and Written Opinion for PCT/US2020/044978, mailed Oct. 26, 2020.
International Search Report and Written Opinion for PCT/US2021/016821 mailed Apr. 26, 2021.
International Search Report and Written Opinion for PCT/US2021/024177, mailed Jun. 23, 2021.
International Search Report and Written Opinion for PCT/US2021/056708, mailed Jan. 27, 2022.
International Search Report and Written Opinion for PCT/US21/42061, mailed Nov. 26, 2021.
International Search Report and Written Opinion for PCT/US21/44532, mailed Jan. 11, 2022.
International Search Report and Written Opinion for PCT/US21/56710, mailed Feb. 23, 2022.
International Search Report and Written Opinion of PCT/US19/57305, mailed Jan. 2, 2020.
International Search Report and Written Opinion of PCT/US20/54117, mailed Dec. 22, 2020.
Joly, "Atmospheric Measurements by Ultra-Light Spectrometer (AMULSE) Dedicated to Vertical Profile in Situ Measurements of Carbon Dioxide ($CO_2$) Under Weather Balloons: Instrumental Development and Field Application," Sensors 2016, 16, 1609.
Khan, "Low Power Greenhouse Gas Sensors for Unmanned Aerial Vehicles", Remote Snse. 2012, 4, 1355-1368.

(56) References Cited

OTHER PUBLICATIONS

Villa. "An Overview of Small Unmanned Aerial Vehicles for Air Quality Measurements: Present Applications and Future Prospectives". Sensors. Web . Jul. 12, 2016.
White, "Development of an Unmanned Aerial Vehicle for the Measurement of Turbulence in the Atmospheric Boundary Layer", Atmosphere, v.8, issue 10, 195, pp. 1-25.
International Search Report and Written Opinion for PCT/US2023/023933 mailed Sep. 26, 2023.
IEEE Conference Paper, "Research of the high pressure jet performance of small size nozzle," ISBN :978-1-5090-1087-5, Publication Date : Oct. 1, 2016, Conference dates Oct. 10, 2016 thru Oct. 12, 2016.[retrieved from the Internet] on Sep. 1, 2023 at 4:14pm.
Lilian Joly, The evolution of AMULSE (Atmospheric Measurements by Ultra-Light Spectrometer) and its interest in atmospheric applications. Results of the Atmospheric Profiles of GreenhousE gasEs (APOGEE) weather balloon release campaign for satellite retrieval validation, p. 1-28, Sep. 25, 2019, Atmospheric Measurement Techniques Discussion (Joly).
International Search Report and Written Opinion for PCT/US19/38015, mailed Oct. 18, 2019.
International Search Report and Written Opinion for PCT/US23/13893, mailed Jun. 30, 2023.
International Search Report and Written Opinion for PCT/US23/23905 mailed Oct. 5, 2023.
International Search Report and Written Opinion for PCT/US22/38951, mailed Nov. 28, 2022.
Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.
Krings et al., Atmos. Meas. Tech., 11, 721-739, Feb. 7, 2018.
Clilverd, Mark A. et al., Energetic particle injection, acceleration, and loss during the geomagnetic disturbances which upset Galaxy 15, Journal of Geophysical Research, vol. 117, A12213, doi: 10.1029/2012JA018175, 2012, pp. 1-16 (Year:2012).
Kem, Christoph et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year:2018).
Liao, J. et al. Observations of Inorganic bromine(HOBr, BrO, and Br2) speciation at Barrow, Alaska in spring 2009, Journal of Geophysical Research, vol. 117, DOOR16, doi:10.1029/2011JD016641, 2012, pp. 1-11 (Year:2012).
Liu, Siwen et al., Development of a UAV-Based System to Monitor Air Quality over an Oil Field, Montana Technological University, Montana tech Library Digital Commons @ Montana Tech Graduate Theses & Non-Theses, Fall 2018, pp. 1-85 (Year:2018).
Miyama, Toru et al., Estimating allowable carbon emission for CO2 concentration stabilization using a GCM-based Earth system model, Geophysical Research Letters, vol. 36,L19709, doi:10.1029/2009GL039678, 2009, pp. 0094-8276 (Year:2009).
Oppenheimer Clive et al., Ultraviolet Sensing of Volcanic Sulfur Emissions, Elements (an Internatioknal Magazine of Mineralogy, Geochemistry, and Petrology), Apr. 2010, vol. 6, pp. 87-92 (Year: 2010).
Parazoo, Nicholas C. et al., Interpreting seasonal changes in the carbon balance of southern Amazonia using measurements of XCO2 and chlorophyll fluorescence from Gosat, Geophysical Research Letters, vol. 40.2829-2833, doi: 10.1002/grl.50452, 2013 pp. 2829-2833 (Year:2013).
Queiber, Manuel et al., A new frontier in CO2 flux measurements using a highly portable DIAL laser system, Scientific Reports, DOI: 10.1038/srep33834 1, Sep. 22, 2016, pp. 1-13(Year:2016).
Queiber, Manuel et al., Large-area quantification of subaerial CO2 anomalies with portable laser remote sensing and 2d tomography, the Leading Edge Mar. 2018, pp. 306-313 (Year:2018).
Feng, Lingbing, Nowak, Gen, O'Neill, T.J., Welsh, A.H."Cutoff; a spatio-temporal imputation method." Journal of Hydrology 519 (2014) : 3591-3605 (Year:2014).
Cabreira et al. "Survey on Coverage Path Planning with Unmanned Aerial Vehicles", published: Drones, published: Jan. 2019, pp. 1-38, year 2019.
Development of a mobile tracer correlation method for assessment of air emissions from landfills and other area sources, Atmospheric Environment 102 (2015) 323-330. T.A. Foster-Wittig et al. 2015.
Measurements of Methane Emissions from Landfills Using a Time Correlation Tracer Method Based on FTIR Absorption Spectroscopy, Environ. Sci. Technol. 2001, 35, 21-25, B. Galle et al. 2001.
Uehara, K: "Dependence of harmonic signals 1-15 on sample-gas parameters in wavelength-modulation spectroscopy for precise absorption measurements", Applied Physics B, Springer Berlin Heidelberg, Berlin/Heidelberg, vol. 67, Jan. 2, 1998, pp. 517-523, XP007921671, ISSN:0946-2171, Doi: 10.1007/S003400050537.
Adame J A et al: "Application of cluster analysis to surface ozone, NOand SOdaily patterns in an industrial area in Central-Southern Spain measured with a DOAS system", Science of the Total Environment, Elsevier, Amsterdam, NL, vol. 429, Apr. 11, 2012 (Apr. 11, 2012), pp. 281-291, XP028491183, ISSN: 0048-9697, DOI: 10.1016/J.SCITOTENV.2012.04.032.
Field Trial of Methane Emission Quantification Technologies, Society of Petroleum Engineers, SPE-201537-MS, Allen et al., Oct. 2020.
Tao Lei et al:" Low-power, open-path mobile sensing platform for high-resolution measurements of greenhouse gases and air pollutants", Applied Physics B, Springer Berlin Heidelberg, Berlin/Heidelberg, vol. 119, No. 1, Mar. 10, 2015 (Mar. 10, 2015), pp. 153-164, XP035445836, ISSN: 0946-2171, DOI: 10.1007/S00340-015-6069-1 [retrieved on Mar. 10, 2015].
Tarsitano C G et al: Multilaser Herriott Cell for Planetary Tunable Laser Spectrometers', Applied Optics , Optical Society of America, Washington, DC, US, vol. 46, No. 28, Oct. 1, 2007 (Oct. 1, 2007), pp. 6923-6935, XP001508502, ISSN:0003-6935, DOI: 10.1364/AO.46.006923.
Coombes et al, "Optimal Polygon Decomposition for UAV Survey Coverage Path Planning in Wind", published: Jul. 2018, publisher: 'Sensors' (Year:2018).
He et al. "Static Targets' Track Path for UAVs Meeting the Revisit Interval Requirement", published :2013, publisher : IEEE (Year:2013).

* cited by examiner

LOCALIZATION ANALYTICS ALGORITHMS AND METHODS

CROSS-REFERENCE TO RELATED APPLICATIONS

This application is a 35 U.S.C § 371 National Stage Entry of International Application No. PCT/US2019/038015 filed Jun. 19, 2019, which claims the priority benefit of U.S. Provisional Patent Application Ser. No. 62/687,152 filed Jun. 19, 2018, incorporated herein by reference in their entirety for all purposes.

FIELD OF ENDEAVOR

Embodiments relate generally to methane concentration measurement, and more particularly to Unmanned Aerial System (UAS) methane concentration measurement.

BACKGROUND

Methane ($CH_4$) is an odorless and colorless naturally occurring organic molecule, which is present in the atmosphere at average ambient levels of approximately 1.85 ppm as of 2018 and is projected to continually climb. While methane is found globally in the atmosphere, a significant amount is collected or "produced" through anthropogenic processes including exploration, extraction, and distribution of petroleum resources in the form of natural gas. Natural gas, an odorless and colorless gas, is a primary source of energy used to produce electricity and heat. The main component of natural gas is methane (93.9 mol % $CH_4$ typ.). While extraction of natural gas is a large source of methane released to atmosphere, major contributors of methane also include livestock farming (enteric fermentation), and solid waste and wastewater treatment (anaerobic digestion).

SUMMARY

In one embodiment, a method disclosed herein may include: receiving, by a ground control station (GCS) having a processor with addressable memory, a plurality of point source gas concentration measurements; receiving, by the GCS, a meteorological data corresponding to each point source concentration gas measurement; determining, by the GCS, if each point source gas concentration measurement may be an elevated ambient gas concentration; generating, by the GCS, a back trajectory for each elevated ambient gas concentration; storing, by the GCS, the position of each generated back trajectory in a grid; determining, by the GCS, a probability of a gas source location corresponding to the stored positions in the grid; and generating, by the GCS, an overlay showing the probability of the gas source location.

Additional method embodiments may include: generating, by one or more gas concentration sensors the plurality of point source gas concentration measurements. In additional method embodiments, the one or more gas concentration sensors are disposed on one or more unmanned aerial vehicles (UAVs). Additional method embodiments may include: receiving, by the GCS, a spatial position of the UAV corresponding to the received point gas source concentration measurement. Additional method embodiments may include: generating, by a weather station, the meteorological data. In additional method embodiments, the meteorological data comprises an instantaneous wind vector, an average wind vector, a wind vector component magnitude variance, and a wind vector component direction variance.

In additional method embodiments, the point source gas concentration measurement may be a methane gas measurement. In additional method embodiments, the generated back trajectory may be generated using a stochastic particle trajectory model. In additional method embodiments, storing the position of each generated back trajectory in a grid may further comprise: summing, by the GCS, the stored position within each cell of the grid. Additional method embodiments may include: normalizing, by the GCS, the stored position of each generated back trajectory in the grid. Additional method embodiments may include: determining, by the GCS, a perimeter of the gas source location based on the normalized stored position of each generated back trajectory.

Additional method embodiments may include: displaying, by the GCS, the generated overlay on a two-dimensional (2D) map. Additional method embodiments may include: displaying, by the GCS, the generated overlay on a three-dimensional (3D) map. In additional method embodiments, the grid may be a two-dimensional (2D) grid. In additional method embodiments, the grid may be a three-dimensional (3D) grid.

In one embodiment, a system disclosed herein may include: a ground control station (GCS) having a processor with addressable memory, the processor configured to: receive a plurality of point source gas concentration measurements; receive a meteorological data corresponding to each point source concentration gas measurement; determine if each point source gas concentration measurement may be an elevated ambient gas concentration; generate a back trajectory for each elevated ambient gas concentration; store the position of each generated back trajectory in a grid; determine a probability of a gas source location corresponding to the stored positions in the grid; and generate an overlay showing the probability of the gas source location.

Additional system embodiments may include: one or more gas concentration sensors, where the one or more gas concentration sensors are configured to generate the plurality of point source gas concentration measurements. Additional system embodiments may include: one or more unmanned aerial vehicles (UAVs), where the one or more gas concentration sensors are disposed on the one or more UAVs. In additional system embodiments, the processor may be further configured to: receive a spatial position of the UAV corresponding to the received point gas source concentration measurement. Additional system embodiments may include: a weather station, where the weather station may be configured to generate the meteorological data. In additional system embodiments, the meteorological data comprises an instantaneous wind vector, an average wind vector, a wind vector component magnitude variance, and a wind vector component direction variance.

In additional system embodiments, the point source gas concentration measurement may be a methane gas measurement. In additional system embodiments, the generated back trajectory may be generated using a stochastic particle trajectory model. In additional system embodiments, the processor may be further configured to: sum the stored position within each cell of the grid. In additional system embodiments, the processor may be further configured to: normalize the stored position of each generated back trajectory in the grid. In additional system embodiments, the processor may be further configured to: determine a perimeter of the gas source location based on the normalized stored position of each generated back trajectory.

Additional system embodiments may include: a display in communication with the GCS, where the display may be configured to show the generated overlay on at least one of: a two-dimensional (2D) map and a three-dimensional (3D) map. In additional system embodiments, the grid may be a two-dimensional (2D) grid. In additional system embodiments, the grid may be a three-dimensional (3D) grid.

In one embodiment, another system disclosed herein may include: an unmanned aerial vehicle (UAV) configured to follow a flight path about one or more potential methane sources, where the UAV may be configured to collect a UAV data; a payload affixed to the UAV, where the payload comprises one or more gas concentration sensors, and where the payload may be configured to measure an ambient methane gas concentration corresponding to the UAV data along the flight path; a weather station configured to measure a meteorological data; a ground control station (GCS) having a processor with addressable memory, where the GCS may be in communication with the UAV, the payload, and the weather station, and where the processor of the GCS may be configured to: receive the measured ambient methane gas concentration corresponding to the UAV data; receive the Meteorological data; determine whether the received ambient methane gas concentration may be an elevated ambient methane gas concentration; determine a probability of a location of the one or more potential methane sources based on elevated ambient methane gas concentration, UAV data, and Meteorological data; and generate a relative probability map of the one or more potential methane sources based on the determined probability of the location of the one or more potential methane sources.

In one embodiment, another method disclosed herein may include: determining, by a ground control station (GCS) having a processor with addressable memory, a flight path of an unmanned aerial vehicle (UAV) about one or more methane sources; measuring, by a payload of the UAV, a methane concentration along the flight path; determining, by an autopilot of the UAV, a UAV information Data Packet comprising at least one of: GPS location, time, barometric pressure, altitude, relative altitude, and/or UAV orientation; generating, by the UAV, a UAV Data Packet comprising the measured methane concentration and the determined UAV information; generating, by a weather station, a Meteorological Data Packet comprising data from at least one of: an anemometer, one or more pressure sensors, a pyranometers, a ground surface temperature sensor, an air temperature sensor a humidity sensor, and soil heat flux plates; receiving, by the GCS, the UAV Data Packet and the Meteorological Data Packet; combining, by the GCS, the UAV Data Packet with a nearest temporal or interpolated or extrapolated Meteorological Data Packet; generating, by the GCS, a spatial map of methane concentration based on the combined data; and generating, by the GCS, the spatial map of the location of one or more emissions sources based on the combined data.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

The following description is made for the purpose of illustrating the general principles of the embodiments discloses herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

The present system and method disclosed herein allows for determining a methane concentration and location of one or more emissions sources based on measurements from one or more sensors of an unmanned aerial vehicle (UAV), UAV data, and weather and/or atmospheric data from one or more sensors of a weather station. The UAV flies in a flight path about one or more methane sources. Data from the one or more UAV sensors, UAV data, and data from one or more sensors of the weather station are combined, stored, and filtered to generate a spatial map of methane concentration and the one or more emissions sources.

The goal of the natural gas production and supply chain is to deliver gas from source production areas to endpoint users without undue loss. Product loss in this context amounts to flaring or venting, intentional or otherwise, of natural gas to the atmosphere. Undue product loss results in uncaptured revenue, an increased environmental footprint, and possible safety hazards for vented emissions. There are many opportunities throughout the natural gas production and supply chain for gas to be released from containment and lost, e.g. pneumatic component venting, maintenance blowdowns, component failures, accidental release, etc. Natural gas production and distribution infrastructure is spatially distributed. Efficient, wide area survey methods are needed to identify, localize, and quantify natural gas releases throughout the system.

The disclosed UAS measures methane concentration along the chosen UAS flight path at high frequency to detect anomalies associated with natural gas releases. These data are reconciled with atmospheric conditions to identify and quantify the mass flow rate of natural gas sources within an inspection area.

Data Transfer Scheme

Figure 1:
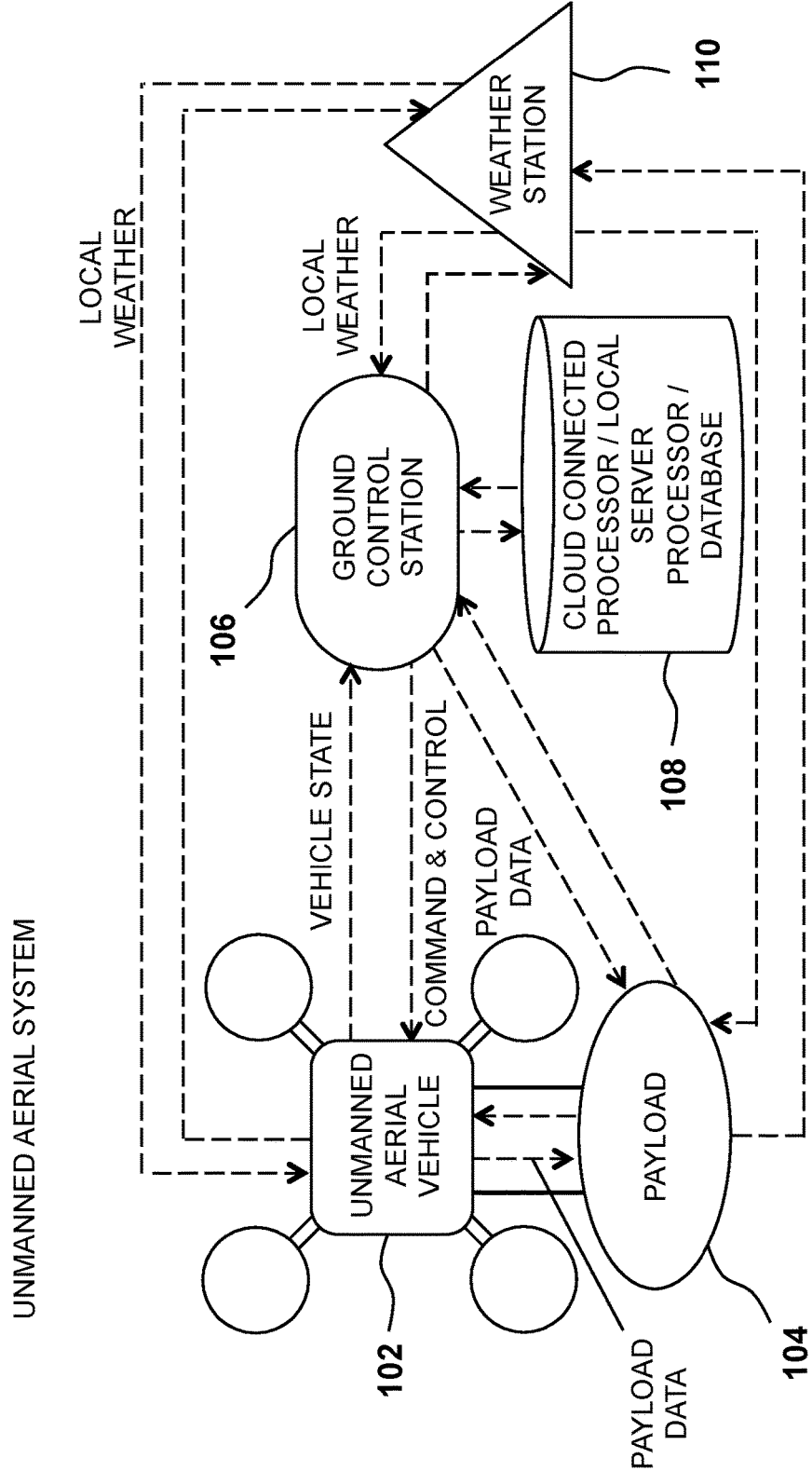
FIG. 1 depicts a data flow in a single sensor and unmanned aerial vehicle (UAV) configuration with a Ground Control Station (GCS) as a point of interface between the UAS and the Cloud Connected Processor, Local Server Processor, and/or Database, according to one embodiment.

FIG. 1 depicts a data flow 100 in a single sensor and unmanned aerial vehicle (UAV) 102 configuration with a Ground Control Station (GCS) 106 as a point of interface between the UAV 102 and the Cloud Connected Processor, Local Server Processor, and/or Database 108, according to one embodiment. The UAV 102 may be a small unmanned aerial vehicle (UAV), with the ability to fly in a three-dimensional flight path in the vicinity of ($\leq$200 m from a $\geq$0.1 SCFH emissions point) potential methane source, and report GPS spatial position. The general flow of data is from one or more gas concentration sensors, i.e., payload 104, affixed to one or more UAVs 102 and wirelessly transmitted to a centralized GCS 106 and transferred to a Cloud Connected Server Processer, Local Server Processor, and/or Database 108. The payload 104 may be an ultra-lightweight, low power, Part per Billion (ppb) sensitivity, mid-Infrared ($\lambda$=3-8 $\mu$m), open path methane concentration sensor with sampling rate>0.1 Hz. A wireless radio or cellular connection may be used for remote data transfer between the UAV 102 and the base station 106 or a cloud server/processor 108. A wireless interface or cellular connection may be used between the base station 106 and/or UAV 102 and a cloud server/processor 108 for performing advanced data analysis functions. Direct, bidirectional data transfer may occur between the UAV and the base station, between the UAV and the cloud processor, and/or between the base station and the cloud processor.

The UAV 102 flight path may be determined on a site-specific basis, using pilot experience and/or self-determined, remote commands. The purpose of the flight path is to measure atmospheric methane background concentration in the vicinity of a possible gas leak, as well as emissions signature (elevated ambient concentration) from all potential sources at the inspection site. High resolution (<0.1 m/s), high frequency measurements (>5 Hz) of wind speed and direction may be made using one or more wind sensors, and one or more additional weather/micro-meteorological sensors including, air temperature, humidity, atmospheric pressure, solar irradiance, ground surface temperature—from the ground, e.g., via a weather station 110, and/or from the UAV 102. The UAV flight path may be determined on a site-specific basis, using a human at the controls and/or self-determined, autonomous control. The purpose of the flight path is to measure gas concentration along a crosswind transect, and vertical profile in the vicinity of a possible gas emissions point. This flight plane is designed to capture the atmospheric methane background as well as emissions signature, i.e., elevated ambient concentration, from all potential sources at the inspection site. A stochastic, back-trajectory model to calculate the receptor sensitivity of the UAS concentration sensor payload and the source location probability. Source emissions data may be displayed on a map, satellite image, aerial image, two-dimensional color map, two-dimensional contour map, and/or three-dimensional topographical surface/mesh.

Figure 2:
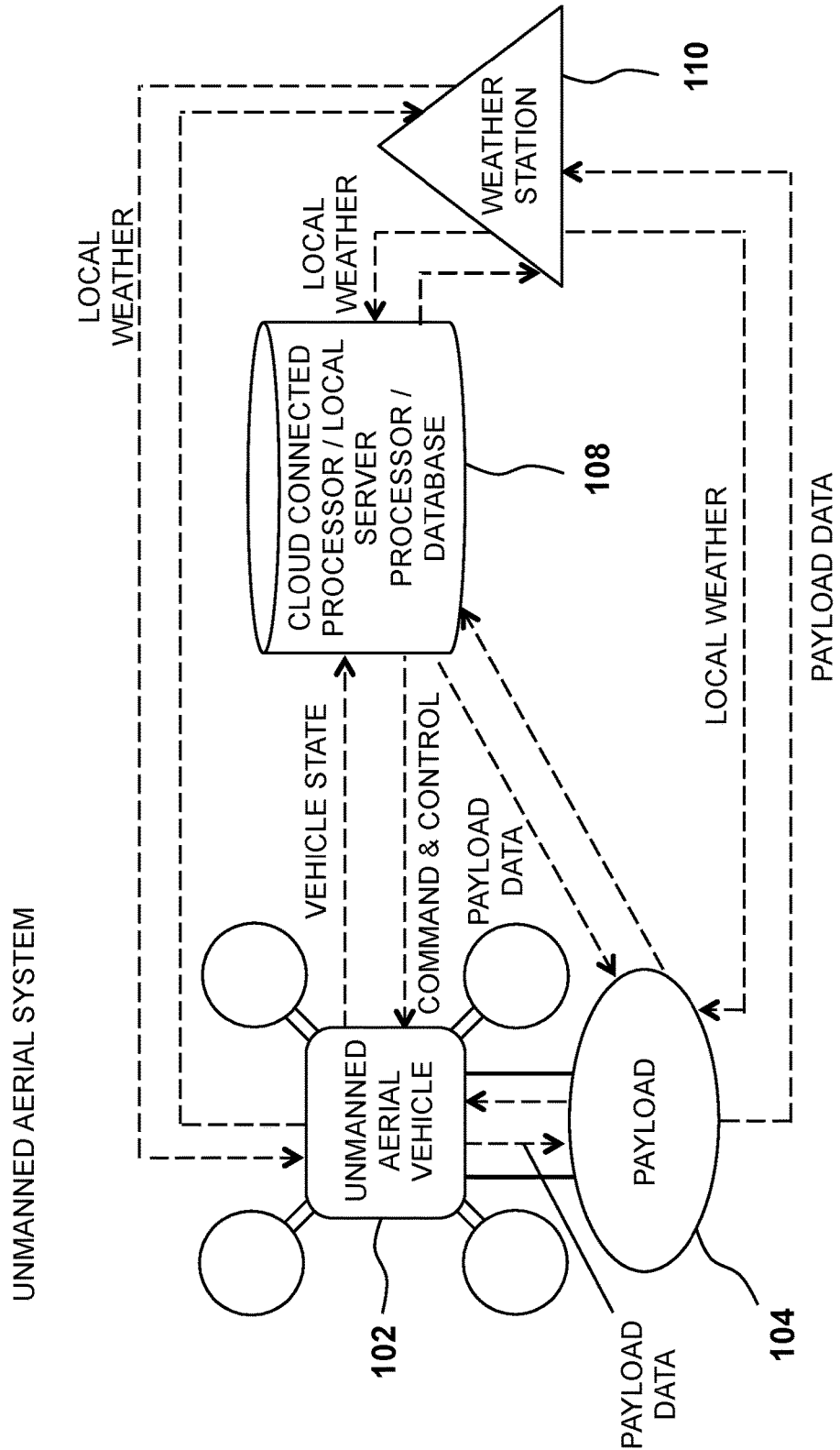
FIG. 2 depicts a data flow in a single sensor and UAV configuration with the UAS directly interfacing with the Cloud Connected Processor, Local Server Processor, and/or Database, according to one embodiment.

FIG. 2 depicts a data flow 200 in a single sensor and UAV configuration with the UAV 102 directly interfacing with the cloud connected processor, local server processor, and/or database 108, according to one embodiment. In another embodiment, the payload(s) 104, UAV(s) 102, and/or weather station(s) 110 communicate directly with a cloud server, processor, local server, processor, and/or database 108. In all cases, each subsystem, e.g., UAV 102; payload 104; GCS, as shown in FIG. 1; cloud server processor, local server processor, and/or database 108; and weather station 110, may or may not have the ability to directly communicate with each other subsystem, which is represented in FIGS. 1-2. At the GCS and/or cloud server processor, local server processor, and/or database 108, the data from the payload 104 is coupled with local weather station 110 data through local private networks and/or publicly available over the internet. The data can then be post-processed on the GCS, as shown in FIG. 1, and/or on a local server and/or on a cloud-hosted server 108.

Figure 3:
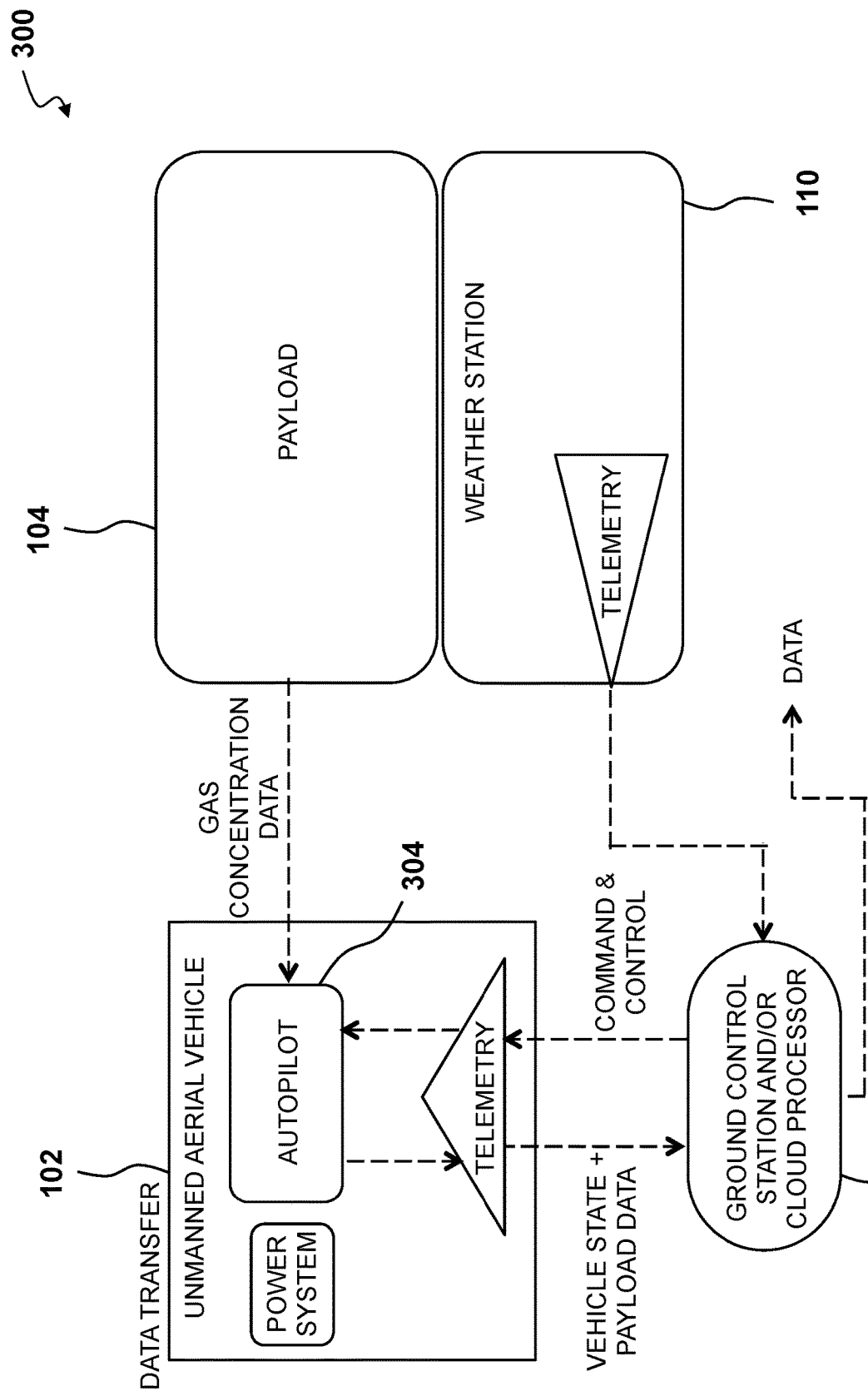
FIG. 3 depicts a detailed data transfer from a single sensor with a single UAV, where this combination of devices comprise a UAS, according to one embodiment.

FIG. 3 depicts a detailed data transfer 300 from a single sensor with a single UAV 102, where this combination of devices comprise a UAS, according to one embodiment. Data from the payload 104 transfers to the UAV 102 and directly to the autopilot 304 via a serial connection. In some embodiments, the data transfer may be via any connection hardwire or wireless. Then, the data is fused with GPS location and time, barometric pressure altitude, relative altitude from LIDAR, Sonar, Radar, and/or UAV orientation, which forms a UAV Data Packet. The UAV Data Packet is transferred to the GCS and/or cloud processor 302 via a 500 mW 915 MHz Frequency Hopping Spread Spectrum (FHSS) transceiver. In some embodiments, the UAV Data Packet may be transferred via any wireless radio. In parallel, a Weather Station 110 having at least an anemometer and which may contain pressure sensors, pyranometers, i.e., solar irradiance, ground temperature sensors, air temperature sensors, and/or any sensors necessary for quantifying current atmospheric conditions forms a Meteorological Data Packet. The GCS and/or cloud processor 302 receives both the Meteorological Data Packet and UAV Data Packet at a frequency greater than 0.1 Hz. Each UAV Data Packet is fused with the nearest temporal or interpolated or extrapolated Meteorological Data Packet and saved on the GCS and/or a cloud processor 302 in an ASCII, binary, or any file necessary.

The data may be uploaded to a cloud server in real-time, near real-time, or at a later time. The data may include: time (GPS or other), latitude, longitude, altitude (barometric or GPS), relative altitude (from LIDAR, Sonar, and/or RADAR), gas concentration, wind vector (x, y, z or x, y), ambient temperature, and/or ambient pressure.

The payload 104 may include a concentration measurement instrument, a gas concentration analyzer, and/or an in situ gas concentration sensor. In some embodiments, the payload 104 may also include a pressure sensor, a temperature sensor, and/or an anemometer.

The weather station 110 may include at least an anemometer. In some embodiments, the weather station 110 may also include a pressure sensor, a pyranometer for solar irradiance, a ground temperature sensor, and an air temperature sensor.

Methodology

Figure 4:
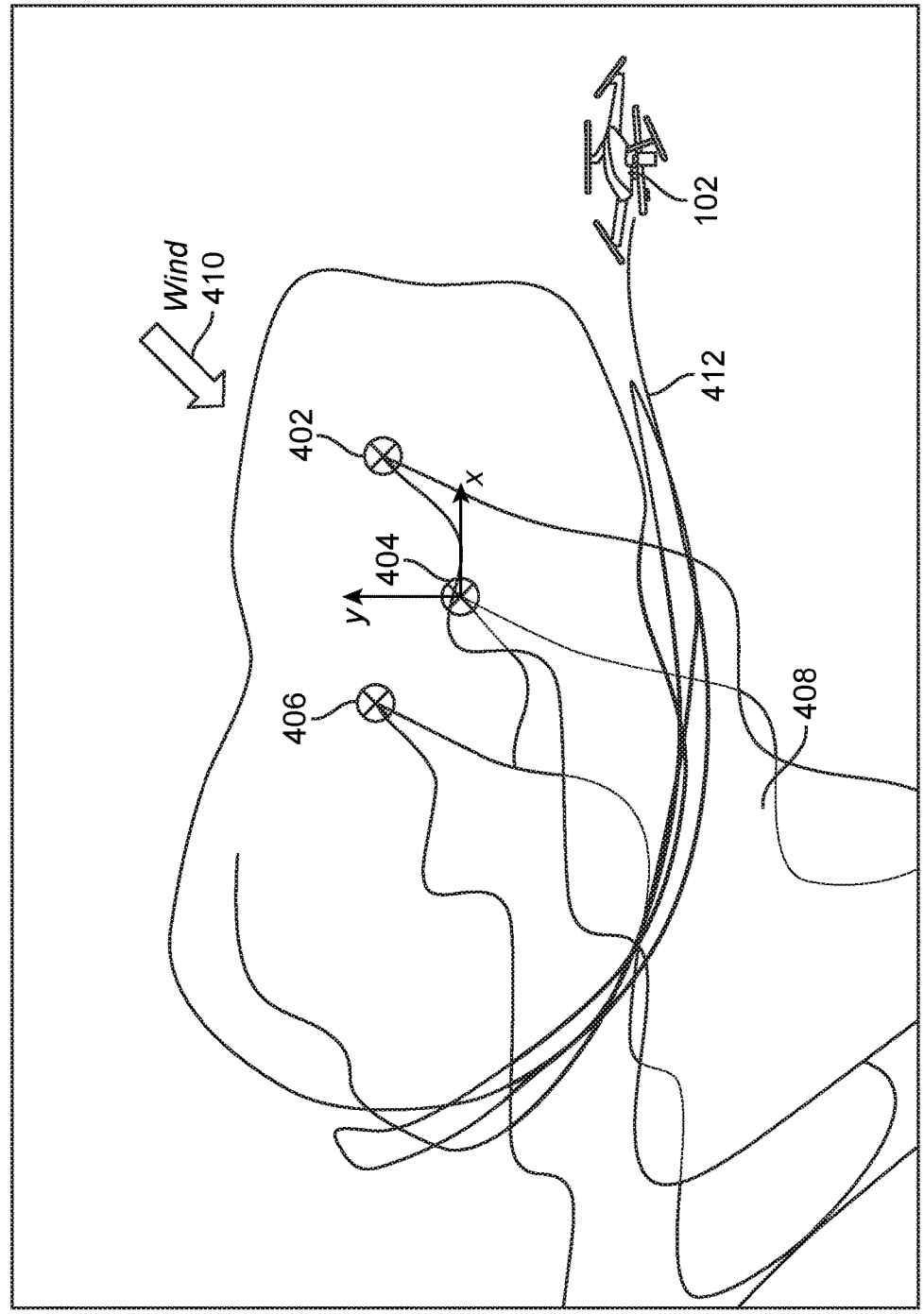
FIG. 4 depicts a plan view illustration of a path for the disclosed UAS for natural gas release detection and localization, according to one embodiment.

FIG. 4 depicts a plan view illustration 400 of a path for the disclosed UAS for natural gas release detection and localization, according to one embodiment One or more natural gas point sources 402, 404, 406 are located within a site boundary, and result in the downwind propagation of natural gas plumes 408 in an average downwind direction 410, which is indicated by an arrow. The UAV 102 traverses a three-dimensional transect 412 and generates a spatial map of methane concentration, i.e., detection, and emissions sources, i.e., localization. This data is analyzed to determine source locations and quantify emission rates using non-parametric regression techniques.

Payload and Flight Path

The UAV payload may be an ultra-lightweight, low power, Part per Billion (ppb) sensitivity, mid-Infrared, open path methane concentration sensor with a sampling rate greater than 0.1 Hz. The UAV flight path is designed to measure the ambient methane concentration in the vicinity of possible source locations within the inspection area. The inspection area may include various natural gas infrastructure components, e.g., wells, valves, tanks, pipelines, compressors, condensers, flares, vents, and the like. The inspection area may also include other areas of possible methane emissions, such as compost facilities, manure collection facilities, livestock containment, landfills, sewer pipelines and vents, abandoned wells, and the like. The UAV flight path is designed based on pilot experience and/or automated input from a search algorithm commanded via autopilot software, as shown in FIG. 3. The goal of the UAV flight path is to position the UAV in as many possible locations on the well pad as possible, both upwind and downwind of all potential and/or observed emission sources. Flight paths may maintain any specified intrinsically safe distance from infrastructure components.

The UAV records and transmits synchronized, $CH_4$ concentration data in volumetric concentration units, i.e., Parts Per Billion Volume (ppbv), and/or pressure and/or temperature and GPS coordinates (latitude, longitude and altitude) via wireless radio to a base station and/or cloud server, as shown in FIGS. 1 and 3. The data is recorded in ASCII, binary, and/or database format on the base station, and synthesized with wind speed and direction data, as well as other Meteorological and/or weather data including air temperature and atmospheric pressure. The combined data is transmitted via wireless radio to a cloud processor for additional advanced analytics and reporting.

Background Calculation and Source Detection

Figure 5:
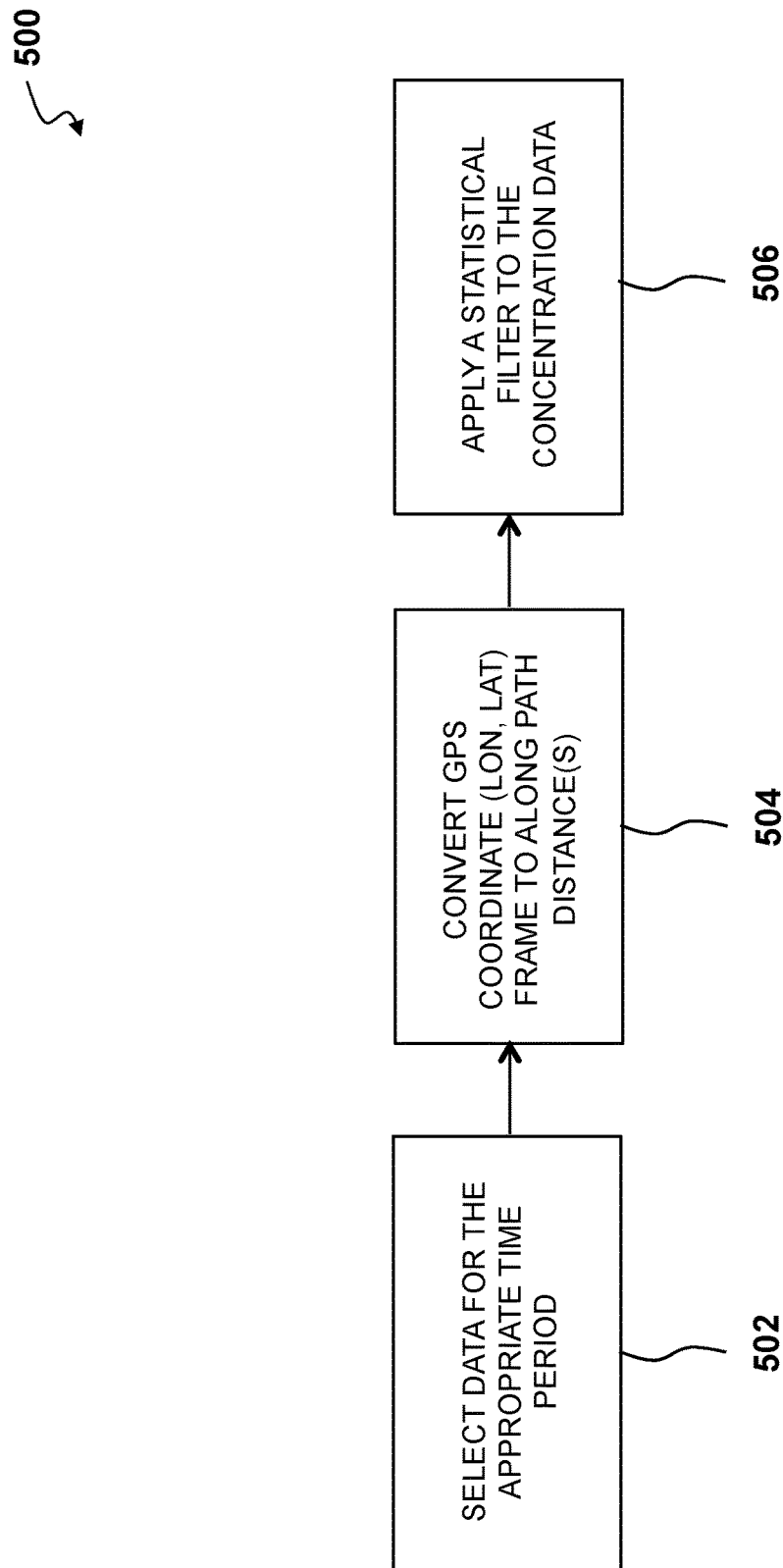
FIG. 5 depicts a background gas concentration workflow, according to one embodiment, according to one embodiment.

FIG. 5 depicts a background gas concentration workflow 500, according to one embodiment. The first step in the localization model is to calculate local background concentration. Typically, it is assumed that the background concentration measured on the upwind side of the source inspection area is a good representation of the local background concentration and provides an estimate of the upwind in-flow condition. Data may be selected for the appropriate time period (step 502). The GPS coordinate, i.e., longitude and latitude, frame is converted to along a path distance (step 504). A statistical filter is applied to the concentration data (step 506).

Figure 6A:
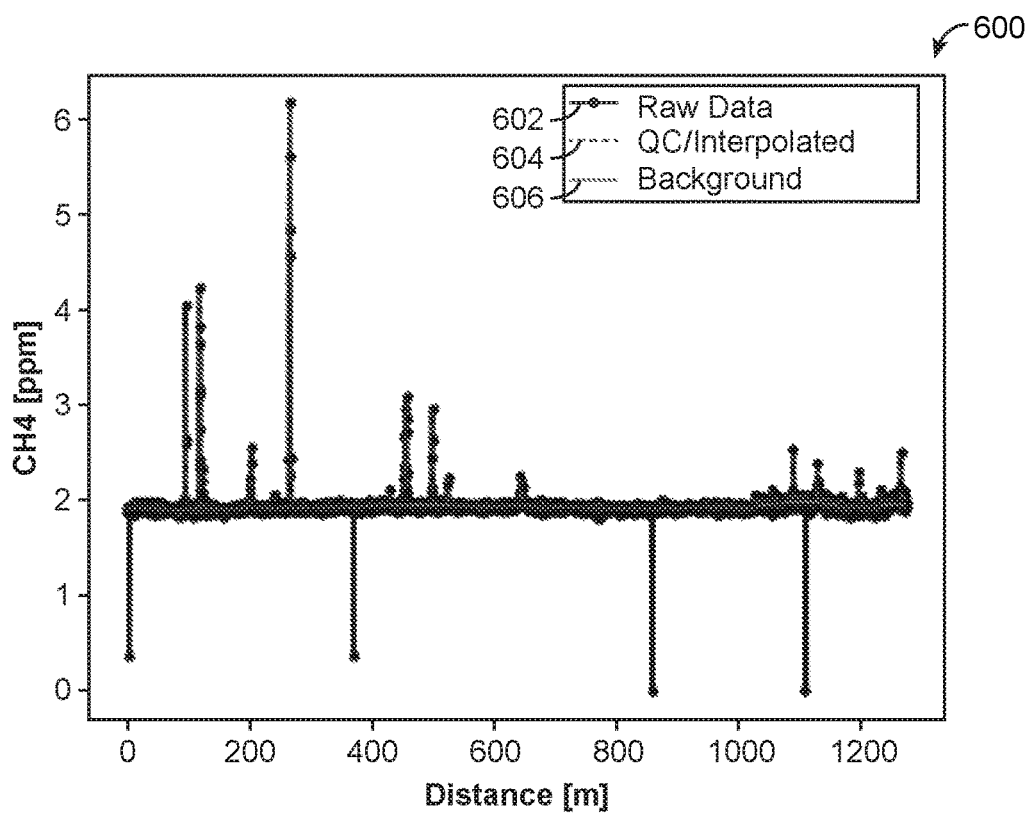
FIG. 6A depicts a graph of raw concentration data, filtered/interpolated data, and a background concentration estimation, according to one embodiment.
Figure 6B:
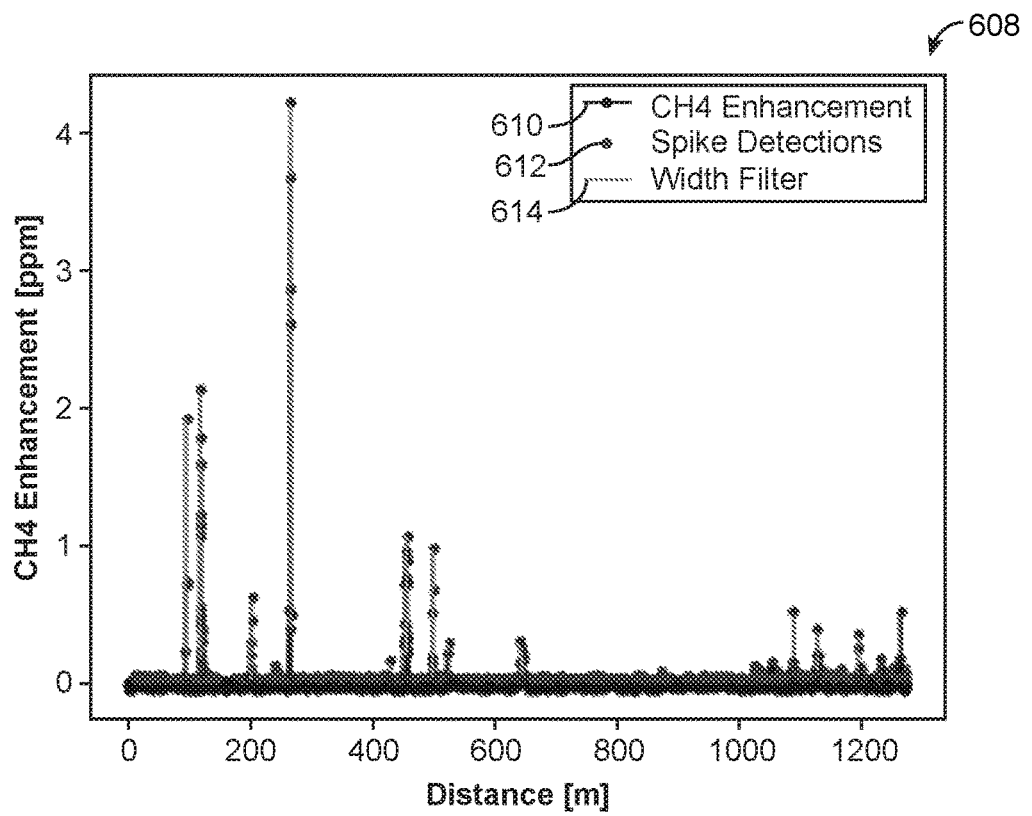
FIG. 6B depicts a graph of concentration enhancement data resolved utilizing the sliding window median filter and spike detection algorithm applied with a width filter, according to one embodiment.

FIG. 6A depicts a graph 600 of raw concentration data 602, filtered/interpolated data 604, and a background concentration estimation 606, according to one embodiment. FIG. 6B depicts a graph 608 of concentration enhancement data 610 resolved utilizing the sliding window median filter and spike detection algorithm 612 applied with a width filter 614, according to one embodiment.

The raw concentration data as a function of distance, e.g., spatial coordinate, is filtered using a sliding window median filter. The filter window scale is determined based on the typical, or expected, gas plume width. For example, if the maximum plume width is expected to be on the order of 10 m, the filter scale would be set to three to five times the max plume width. The median filter also removes infrequent transients, or dropouts, in the concentration measurement caused by communication interference, or platform vibrations. The background concentration 606 is subtracted from the total concentration 602 to obtain the concentration enhancement 610. The concentration enhancement signal contains the signature of an upwind emission source, and quantifies the emissions released by the local source.

A statistical filter is then applied to the concentration enhancement signal 610 to identify "spikes" 612 in the data that indicate methane plumes from nearby sources. The statistical filter determines the Cumulative Distribution Function (CDF) for the concentration enhancement, and targets extremum data points based on a prescribed percentile threshold. The selected points are then analyzed for contiguity and consolidated to form spatially continuous events. Each spike event may be further analyzed according to other metrics such as spatial extent, amplitude, magnitude, variance, and waveform shape. Individual spike events may be included or excluded through a selection process based on these derived quantities.

Wind and Weather Data Calculation

Figure 7:
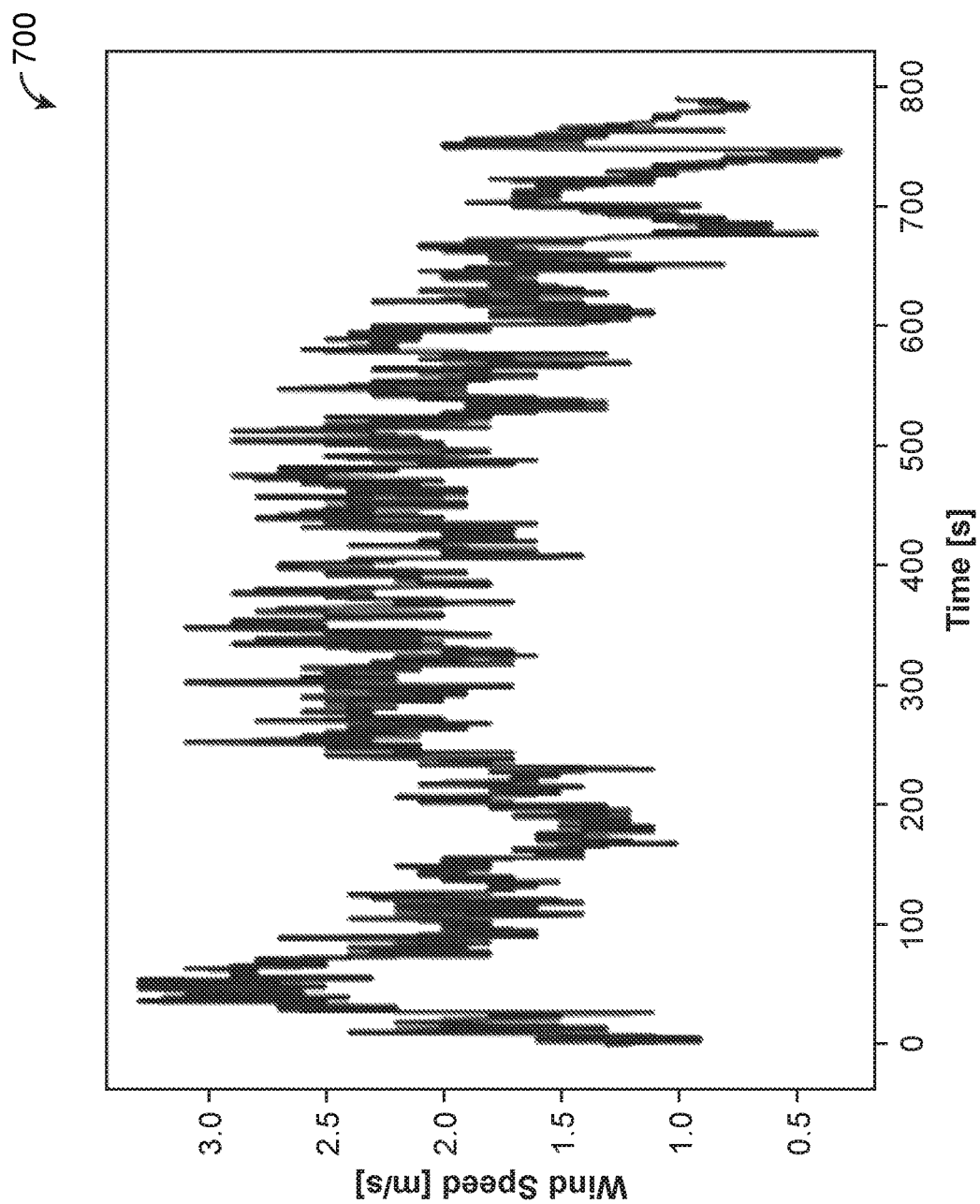
FIG. 7 depicts a graph of typical wind values collected, according to one embodiment.

FIG. 7 depicts a graph 700 of typical wind values collected, according to one embodiment. Wind vector, i.e., a three-component magnitude and direction, is measured continuously, and concurrently over the duration of the UAV flight. Wind measurements may be performed using one or more stationary wind sensors connected to a ground station. Or the wind measurement may be made on-board the UAS during the flight. Additional weather sensors may be included with the ground station to quantify air temperature and pressure.

Spike events that were identified based on a statistical analysis of $CH_4$ concentration data are correlated with wind vector measurements and processed to obtain statistics of wind speed and direction during the detection of each plume.

Figure 8:
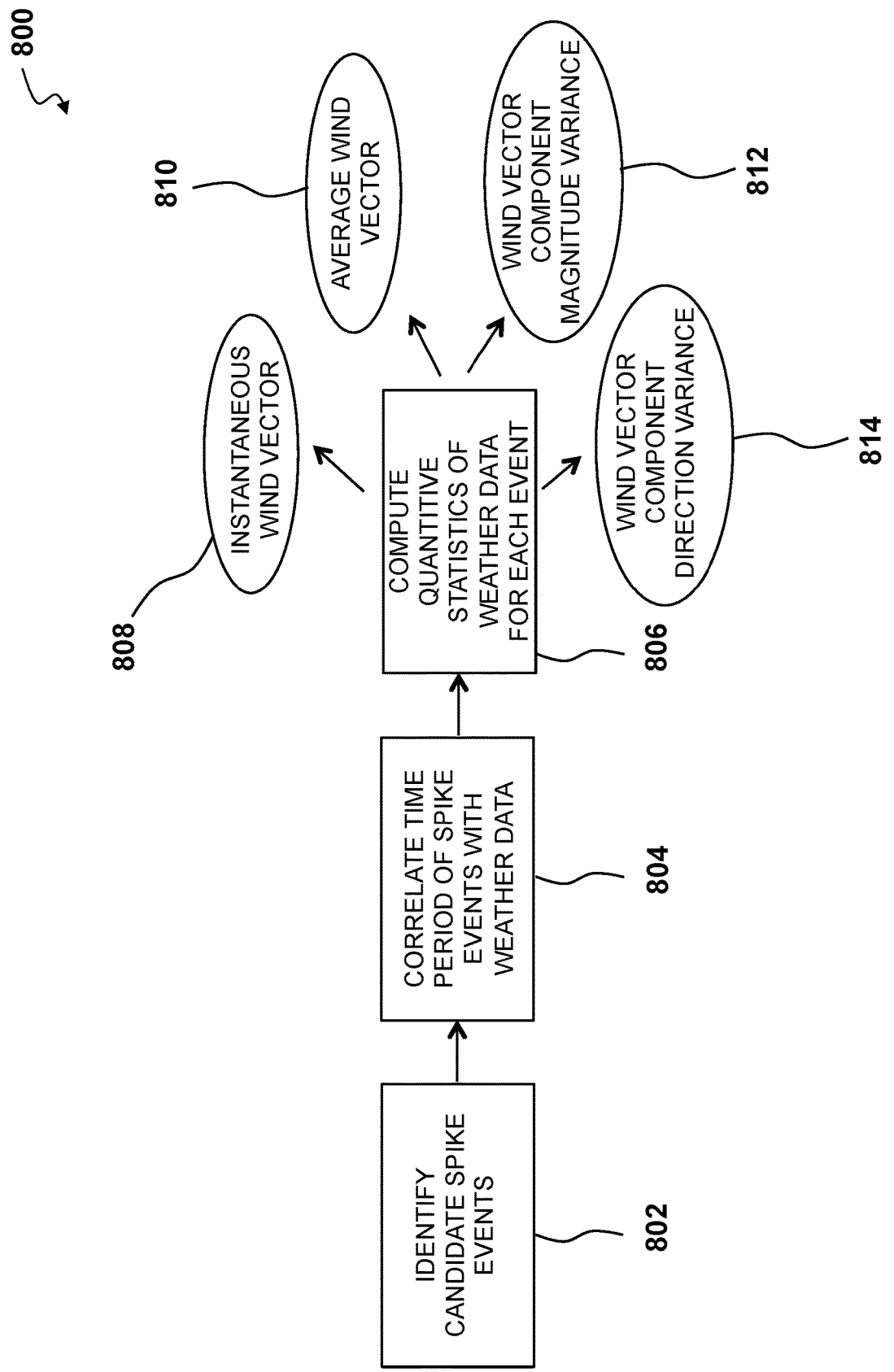
FIG. 8 depicts a workflow for spike identification and statistical analysis of atmospheric conditions.

FIG. 8 depicts a workflow 800 for spike identification and statistical analysis of atmospheric conditions, according to one embodiment. The wind statistics are then applied to determine the approximate location of a detected methane source using an inverse stochastic dispersion model. Meteorological and/or Weather data including air temperature, humidity, atmospheric pressure, solar irradiance, ground surface temperature may be applied to develop a model for local turbulence characteristics and quantify the spatial decorrelation of the wind. This approach is used to quantify the relationship between in situ wind measurements that are made some distance away from the probable source locations, and the actual winds and turbulence occurring at or near the source.

Candidate spike events are identified (step 802). The time period of the spike event is correlated with weather data (step 804). Qualitative statistics of weather data for each event are computed (step 806). The computed qualitative statics (step 806) determine an instantaneous wind vector 808, an average wind vector 810, a wind vector component magnitude variance 812, and/or a wind vector component direction variance 814.

Statistical Inverse Model for Source Location Footprint

Figure 9:
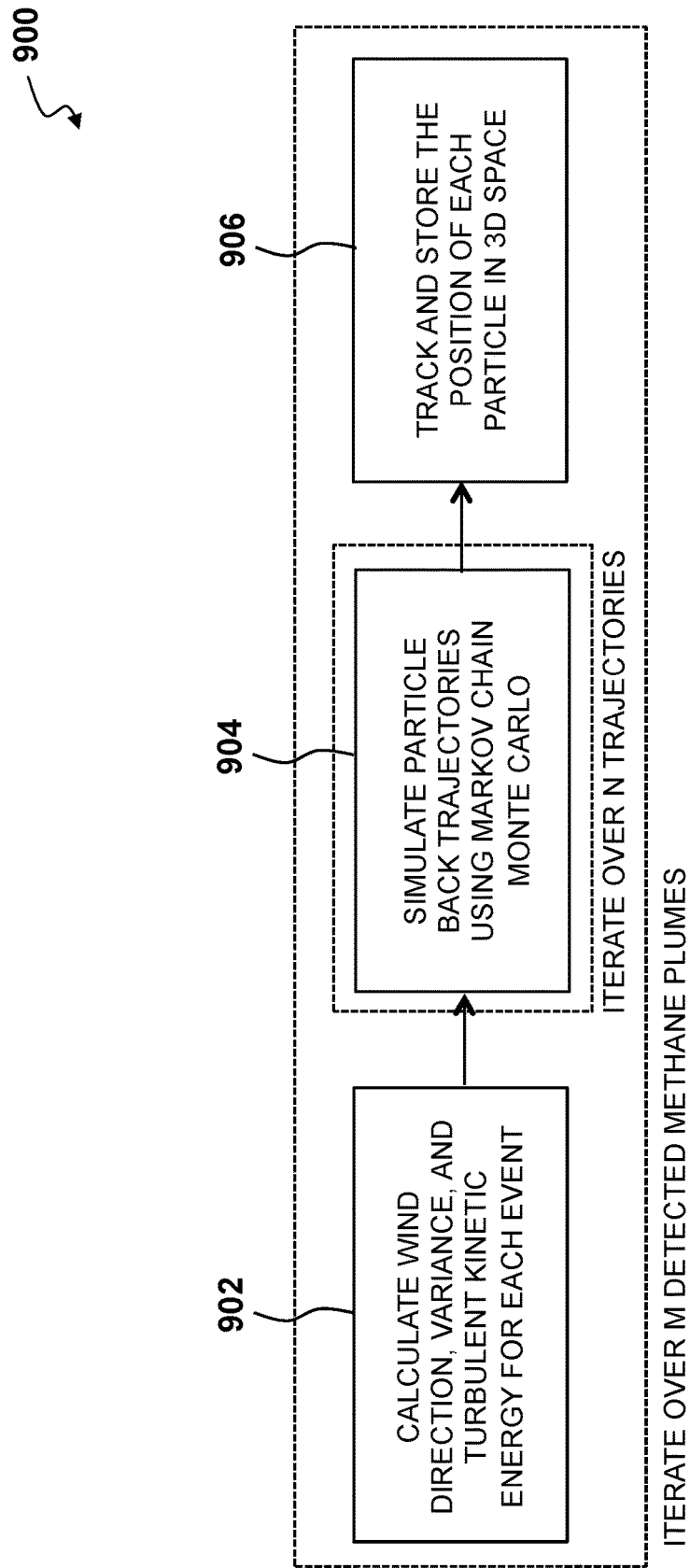
FIG. 9 depicts a back trajectory workflow taking account atmospheric statistics, MCMC particle back trajectory simulation and localization in 3D space into account, according to one embodiment.

FIG. 9 depicts a back trajectory workflow 900 taking account atmospheric statistics, Monte Carlo Markov Chain (MCMC) particle back trajectory simulation and localization in 3D space into account, according to one embodiment. An inverse stochastic dispersion model is applied to determine the probable location of a methane source or sources based on wind statistics measured during each plume event. An inverse dispersion model applies statistics of wind speed, direction, and turbulence to simulate upwind trajectories of massless particles, or air parcels, arriving at a specified downwind sensor location. After stochastically simulating many particle trajectories, the upwind distribution of particle positions provides an estimate of the sensor footprint. The footprint represents the spatial probability that a source of a given magnitude in any location within the model domain would have been detected by the sensor. When applied to individual plume events the inverse model predicts the most probable locations for the source(s) associated with the observed concentration enhancement. When data for many events are combined localization of sources to spatial regions on the order of 0.5-1000 m² is achieved through convergence of the ensemble particle trajectories.

Wind direction, variance, and turbulent kinetic energy for each event are calculated (step 902). This calculation (step 902) is iterated over M detected methane plumes. Then, the particle back trajectories are simulated using Markov Chain Monte Carlo (step 904). This simulation (step 904) is iterated over N trajectories. Then, the position of each particle in 3D space is tracked and stored (step 906). The workflow 900 includes Eqs. 1-3, as discussed below. 3D space may include x, y positions used on a 3D map in some embodiments. In other embodiments, a 3D probability map, e.g., x, y, z, may be created for source location probability.

Figure 10:
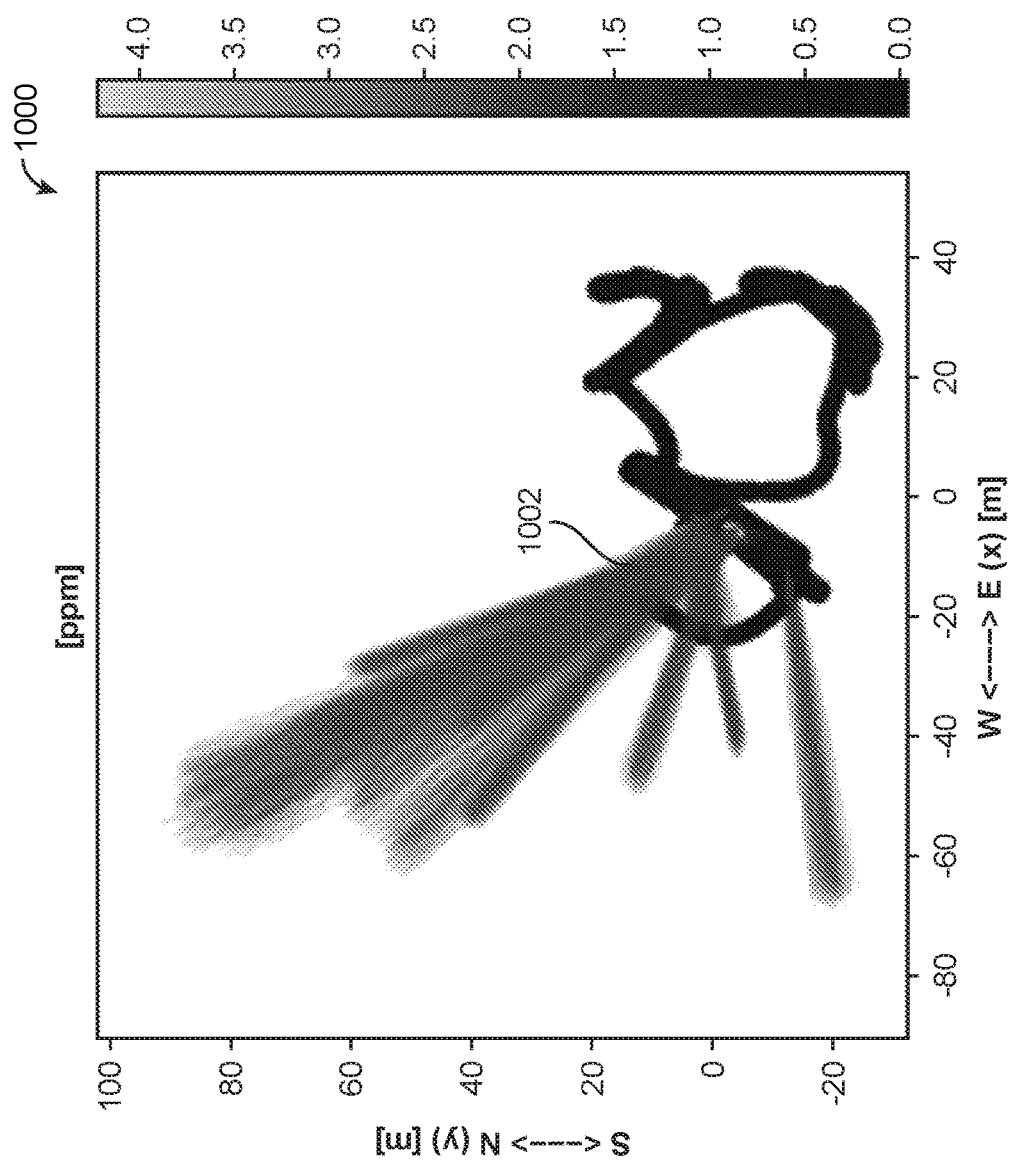
FIG. 10 depicts a graph showing a UAV trajectory according to measured gas concentration enhancements and stochastic particle back trajectories, projected onto a cartesian (x,y) plane, according to one embodiment.

FIG. 10 depicts a graph 1000 showing a UAV trajectory according to measured gas concentration enhancements and projected to the (x,y) plane, according to one embodiment. Particle trajectories 1002 are shown as back-trajectories simulated using MCMC and the Langevin Equation. Each particle trajectory 1002 is created by a stochastic particle trajectory model or stochastic particle back trajectory model, such as shown in Eq. 1. Upwind trajectories are modeled according to a Langevin Equation stochastic differential equation using a MCMC method. In this model, the upwind position of the particle at each timestamp depends on the current position of the particle, the average wind speed and direction, and a random component which is parameterized in terms of the turbulent kinetic energy. Equation 1 shows a form of the Langevin Equation used to compute the particle back trajectory. In Eq. 1 $x_i$ is the vector representing the position of the back trajectory at time t, v is the advective velocity vector, η is a stochastic random variable, κ is the turbulent kinetic energy, and A is scaling parameter which depends on the position of the particle at any given time and other aspects of the turbulent velocity field. v and η are vector quantities of 3-dimensional space.

$$\frac{d\vec{x}_i(t)}{dt} = \vec{v}(x, y, z, t) + A(x, y, z)\sqrt{\kappa}\vec{\eta}(t) \qquad \text{Eq. 1}$$

The path of each parcel back trajectory is determined by solving Equation 1 iteratively using an Euler method and substituting measured values of v, η, κ and A during each plume event. Several hundred particle back-trajectories are derived from independent realizations of Eq. 1 for each plume event and tracked backward in space over a specified time interval. Because each individual particle trajectory is independent of the others, the solution to Eq. 1 is readily distributed in a shared CPU architecture across many processors. When very large simulations are completed near 1:1 speed up can be achieved by distributing the calculation of individual particle trajectories in across many processors. An additional computational advantage of Eq. 1 is that it does not rely on a spatially regular grid, and solutions to particle trajectories are solved on an unstructured grid. This substantially reduces memory usage of the algorithm. Stochastic particle trajectory models in place of Eq. 1 are possible and contemplated.

Figure 11:
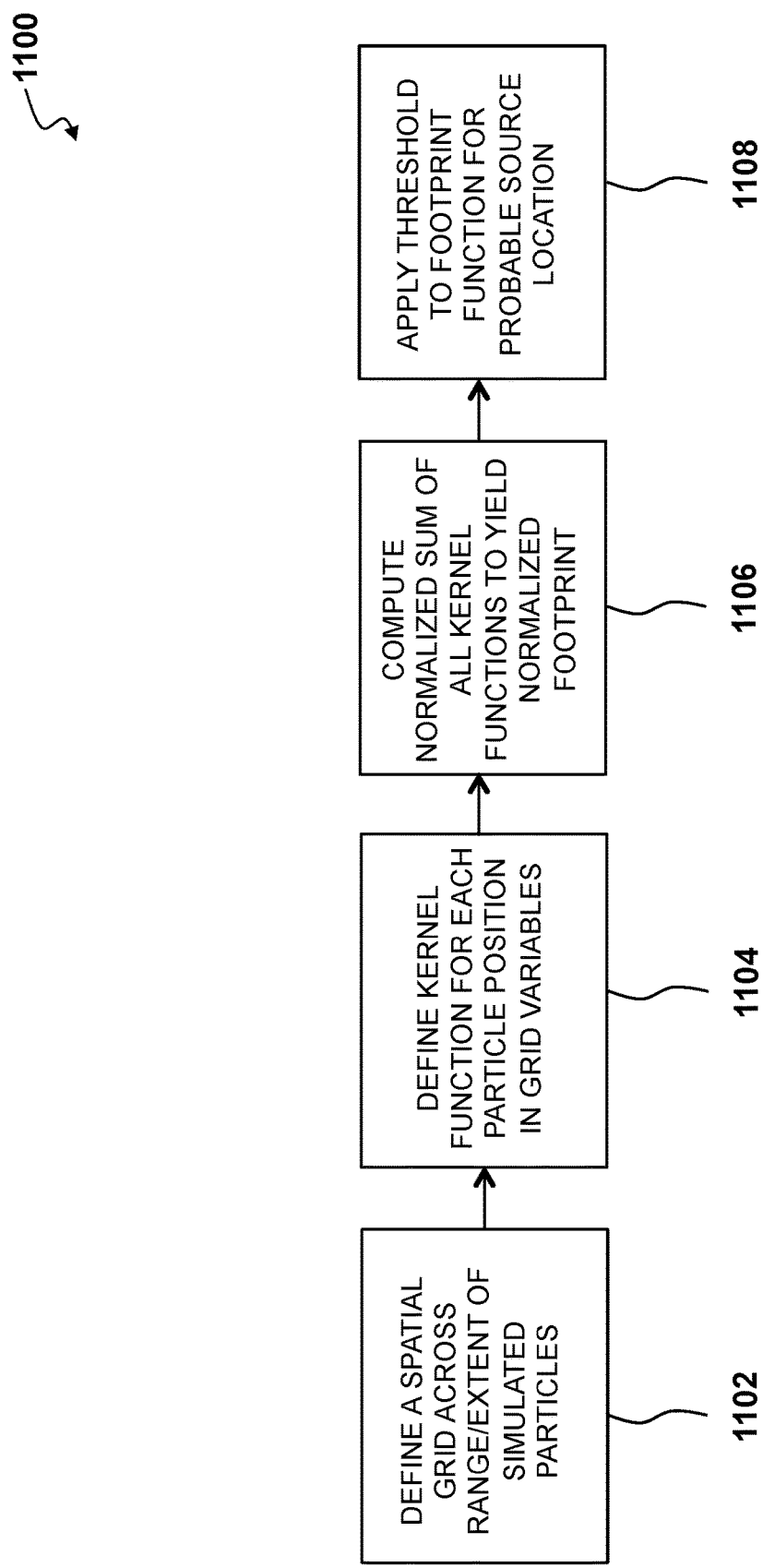
FIG. 11 depicts a workflow for a generating a spatial map of probable source location or locations, according to one embodiment.

FIG. 11 depicts a workflow 1100 for a localization clustering, according to one embodiment. After particle trajectories are determined the spatial footprint of the sensor, weighted over all the methane plumes that were detected, is calculated on a regular grid. A spatial grid is defined across a range/extent of simulated particles (step 1102). Each kernel function is defined for each particle position in grid variables (step 1104). The normalized sum of all kernel functions is computed to yield a normalized footprint (step 1106). Thresholds are applied to the footprint function for probable source location (step 1108). The workflow 1100 includes Eqs. 4-6, as discussed below.

The grid is defined in terms of a fixed coordinate system, which may be Cartesian, spherical, or following a geodesic approximation. The position of each particle at time t is represented on the grid as a kernel. An example of a typical Gaussian kernel p(x,y,z) is shown in Eq. 2, where μ and σ are parameters in the model and $x_0$, $y_0$, $z_0$ a define the location of the maximum value of the Gaussian. Eq. 2-3 show a Monte Carlo simulation using Gaussian kernel. Other simulations are possible and contemplated.

$$p(x, y, z) = \frac{1}{2\pi\sigma_x\sigma_y\sigma_z}\exp \qquad \text{Eq. 2}$$

$$\left\{-\left[\frac{(x-\mu_x)^2}{2\sigma_x^2}\right] - \left[\frac{(y-\mu_y)^2}{2\sigma_y^2}\right] - \left[\frac{(z-\mu_z)^2}{2\sigma_z^2}\right]\right\} - x_0 - y_0 - z_0$$

$$p(\vec{X}, t)_i = \frac{1}{2\pi\sigma^2}\exp\left\{-\left[\frac{(\vec{X}-\vec{\mu})^2}{2\sigma^2}\right]\right\} - \vec{x}_i(t) \qquad \text{Eq. 3}$$

The kernel function is calculated for each independent trajectory and at each timestep (Eq. 3), then summed to generate the cumulative footprint function (Eq. 4). Eqs. 4-6 relate to generating the probability map. The cumulative footprint function describes the probability that the source is in a given location within the simulation domain based on all the methane plume events identified by the disclosed UAS system.

$$f(\vec{X}) = \frac{1}{NM} \sum^{N*M} p(\vec{X}, t)_i \qquad \text{Eq. 4}$$

After the footprint is calculated, the source location area is determined by applying a threshold $\tau$ to the source location probability (Eq. 5). The threshold may be set based on a determined value. In some embodiments, the threshold may be tuned manually. For example, the entire grid shown in FIG. 12 may have a non-zero probability. Applying the threshold may constrain the probability down to the overlay 1302 shown in FIG. 13. The source location probability function may be further modified using a power parameter $\beta$ to enhance the probability gradient in the predicted source area. The power parameter $\beta$ may be used to scale the gradient to increase the rate of change of the gradient. The power parameter $\beta$ may be used to create a larger difference between the minimum probability and the maximum probability. Smaller variations may be enhanced and larger changes may be lessened. The power parameter $\beta$ may be tunable in some embodiments, such as based on wind conditions, environmental factors, or the like. The perimeter of the source location area can also be calculated to provide a spatially uniform source location prediction (Eq. 6).

$$l(\vec{X}) = \begin{cases} f(\vec{X})^\beta; f > \tau \\ 0; f \le T \end{cases} \qquad \text{Eq. 5}$$

$$\partial l(\vec{X}) \qquad \text{Eq. 6}$$

Figure 12:
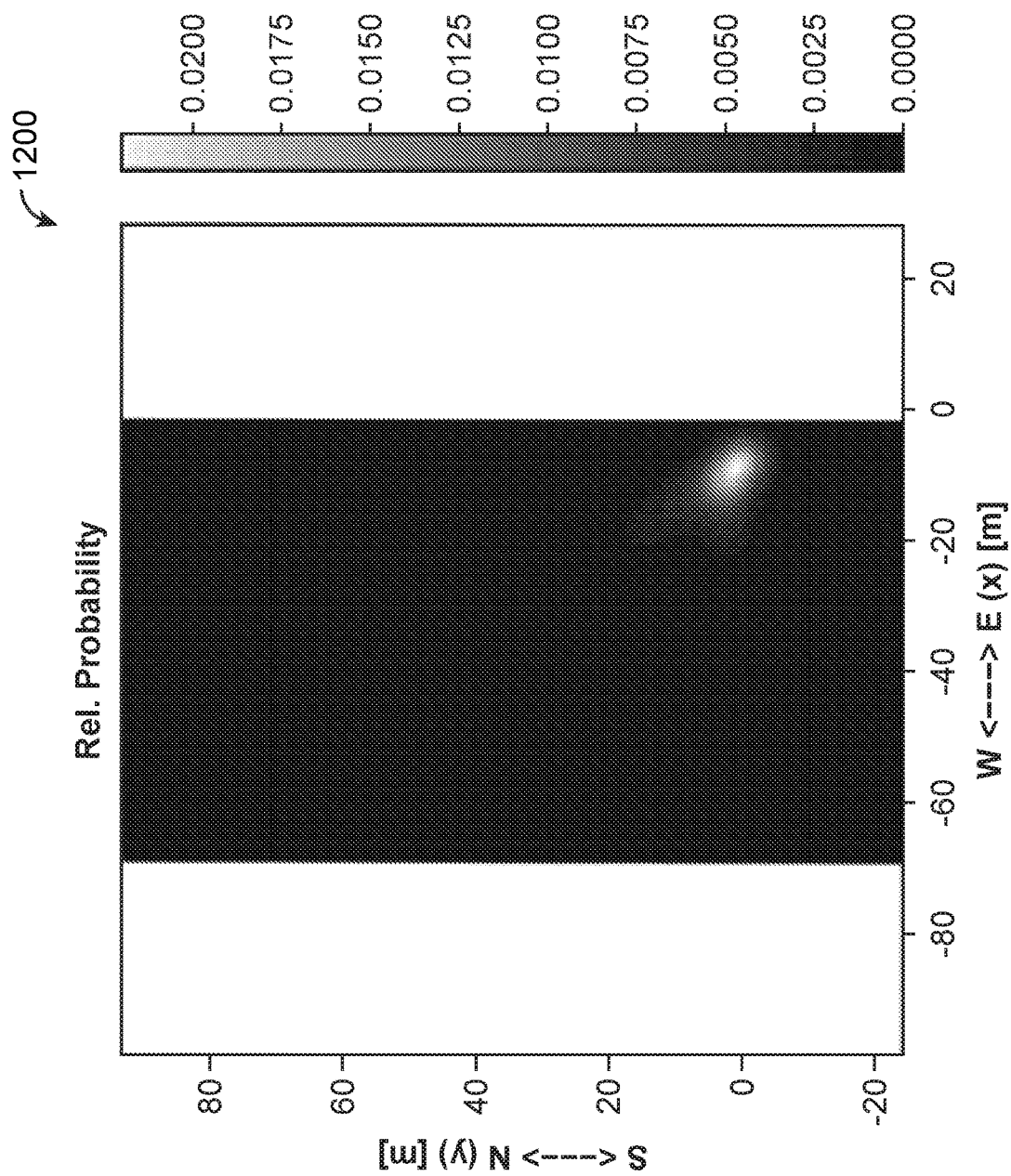
FIG. 12 depicts a relative probability map of emissions source location or locations, according to one embodiment.

The result is a three-dimensional probability map, shown in FIG. 12. FIG. 12 depicts a relative probability map 1200 of emissions source location (x,y,P), according to one embodiment. Each particle trajectory is created by a stochastic particle trajectory model and mapped to a cell on the grid. The density of each cell in the grid, e.g., counting the number of particles in each grid, is used to create the relative probability map 1200.

Map of Source Location Probability

Figure 13:
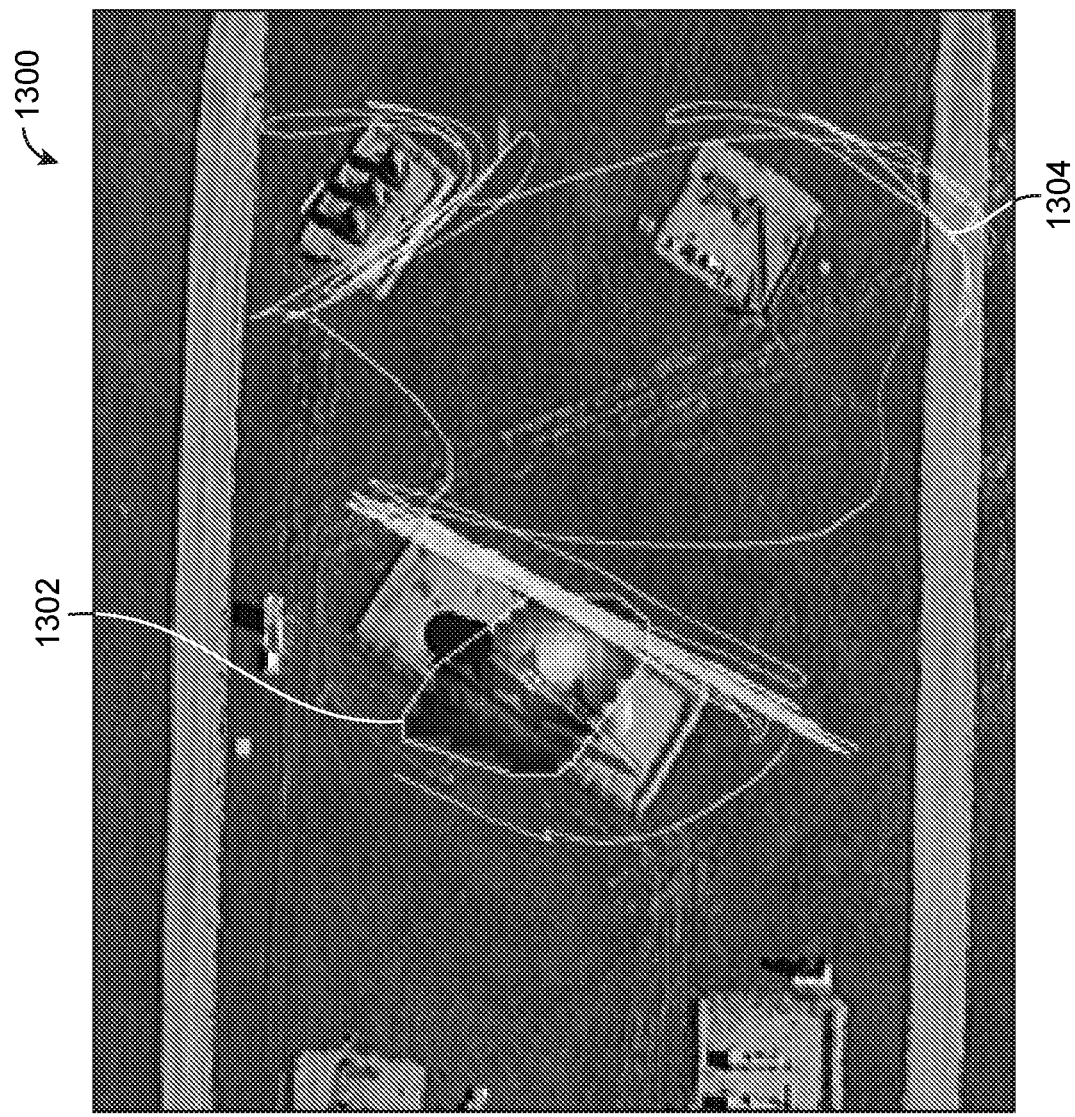
FIG. 13 depicts an aerial map with a relative probability overlay, according to one embodiment.
Figure 14:
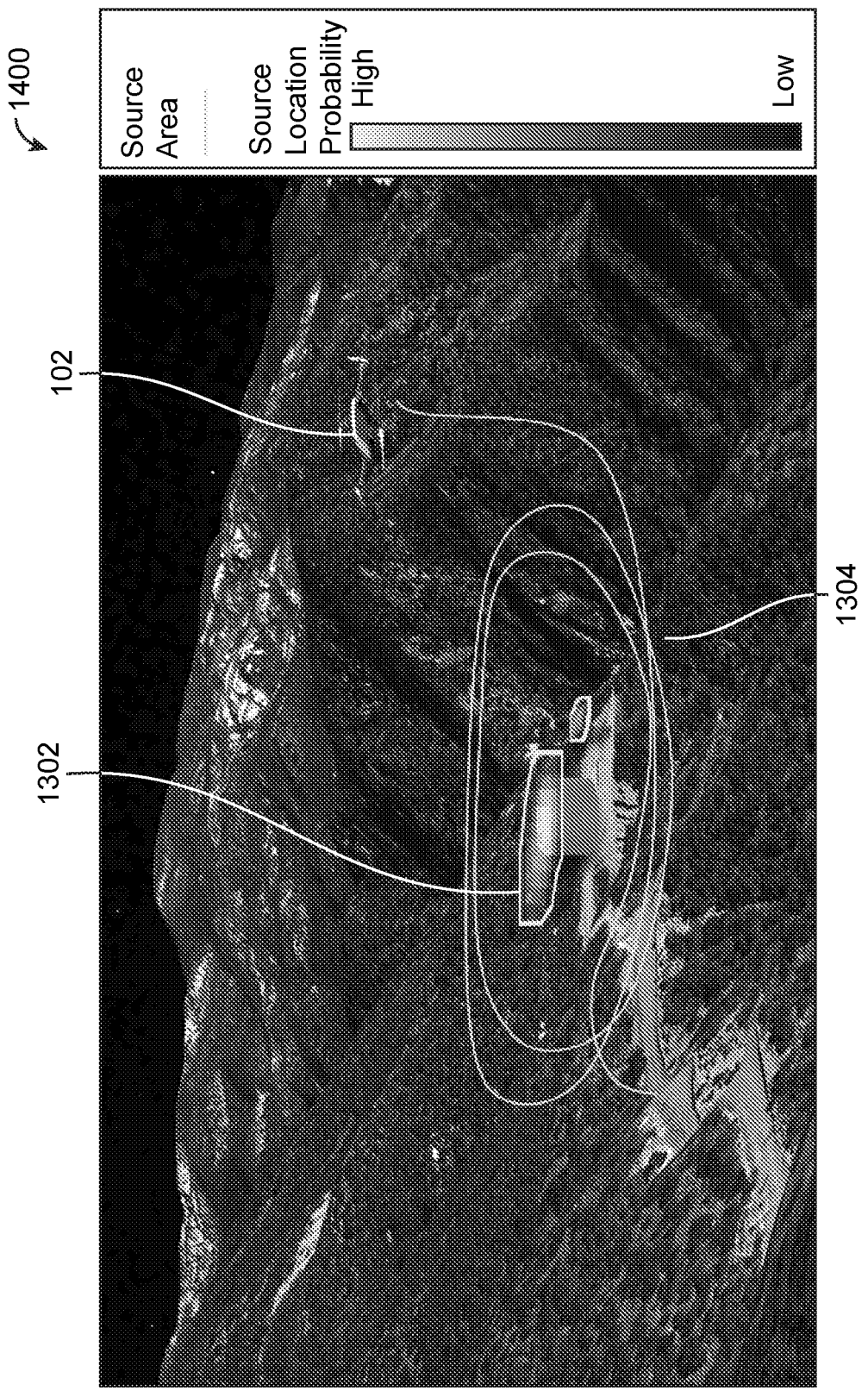
FIG. 14 depicts a three-dimensional illustration of the disclosed UAS system and process for methane source detection and localization, according to one embodiment.

FIG. 13 depicts an aerial map 1300 with a relative probability overlay 1302, according to one embodiment. FIG. 14 depicts a three-dimensional illustration 1400 of the disclosed UAS system and process for methane source detection and localization, according to one embodiment. The UAV 102 flight trajectory 1304 is projected onto overlay 1302 and illustration 1400. The UAV 102 measures point source gas concentration measurements as it flies the flight path 1304. Each measured gas concentration along the flight path 1304 has a stochastic particle trajectory model applied to determine a potential source for elevated gas concentrations. The potential sources are combined in a grid to create the overlay 1302 showing the probability of the gas source location. The overlay 1302 may have an area of highest probability surrounded by areas of lower probability. The flight path 1304 may be any flight path that is downwind of the potential gas source.

The source footprint, localization probability, source location boundary areas are geo-referenced and displayed visually on a map for data reporting purposes. The base map may include a variety of styles including basic street maps, satellite images, and high resolution aerial images, as shown in FIGS. 13-14. FIG. 14 depicts a three-dimensional view of the overlay 1302. In addition to displaying the source location areas, the UAS vehicle path is also shown to indicate the flight path with in the inspection area and identify areas where no sources were detected. The map may also include other features including information about the mass flow rate of the source, wind direction indicators, a distance scale, and a compass rose.

Figure 15:
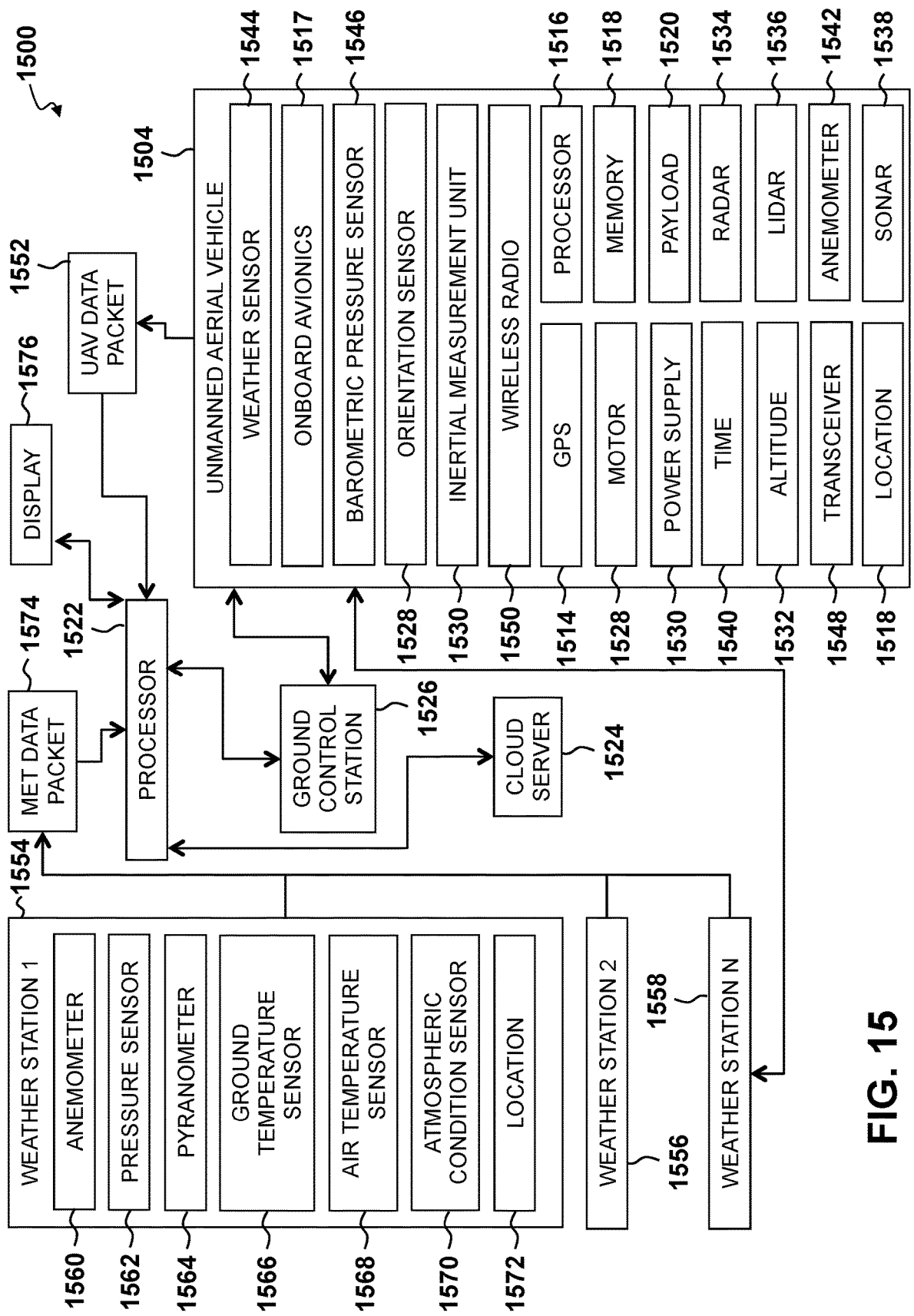
FIG. 15 depicts a high-level block diagram of a UAS system and process for methane source detection and localization, according to one embodiment.

FIG. 15 depicts a high-level block diagram of a UAS system 1500 and process for methane source detection and localization, according to one embodiment. The system 1500 may include a UAV 1504. In some embodiments, the UAV 1504 may be a quadcopter-style aerial vehicle capable of hovering and flying a flight path. In other embodiments, the UAV 1504 may be a winged aerial vehicle. The UAV 1504 may have any number of rotors, motors 1528, wings, or the like to sustain flight and fly the determined UAV flight path. The UAV 1504 may have the ability to fly in a three-dimensional flight path in the vicinity of a potential methane or other gas source.

Embodiments of the unmanned aerial vehicle 1504 may include any number of sensors shown in FIG. 15 based on the desired data. Embodiments of the weather station 1554 may include any number of sensors shown in FIG. 15 based on the desired data. In some embodiments, the weather station 1554 may only include an anemometer 1560. In other embodiments, the weather station 1554 may be integrated into the unmanned aerial vehicle 1504. For example, the anemometer 1560 may be integrated on the unmanned aerial vehicle 1504. In another embodiment, the weather station 1554 may be located on another aerial vehicle or unmanned aerial vehicle. For example, the system may include two or more unmanned aerial vehicles where at least one unmanned aerial vehicle is recording methane gas concentrations and at least one unmanned aerial vehicle is recording meteorological data. The weather station 1554 may be stationary or mobile. The weather station 1554 may be in relatively close proximity to the unmanned aerial vehicle 1504. In some embodiments, the weather station 1554 may record meteorological data. In some embodiments, the weather station 1554 may be from a third-party source, such as a third-party sensor. In some embodiments, the weather station 1554 may predict future meteorological measurements. The nearest temporal Meteorological (MET) data packet 1574 may be combined with the UAV data packet 1552. The frequency of each of the MET data packet 1574 and the UAV data packet 1552 may be different but close in some embodiments. The frequency of each of the MET data packet 1574 and the UAV data packet 1552 may be substantially the same in some embodiments.

The UAV 1504 may have a global positioning system 1514, an onboard avionics 1517, and/or a location sensor 1518 to track a spatial position of the UAV 1504 as it travels along the flight path. The UAV 1504 may track its spatial position as it measures gas concentrations along the flight path such that each gas measurement of the UAV 1504 corresponds to a spatial position where that gas measurement was taken. The global positioning system 1514, onboard avionics 1517, and/or location sensor 1518 may be in communication with a UAV processor 1516 having addressable memory 1518. In some embodiments, the location of the UAV 1504 may be determined by the onboard avionics 1517. The onboard avionics 1517 may include a triangulation system, a beacon, a spatial coordinate system, or the like. The onboard avionics 1517 may be used with the GPS 1514 and/or location sensor 1518 in some embodiments. In other embodiments, the UAV 1504 may use only one of the GPS 1514, the onboard avionics 1517, and/or the location sensor 1518.

The UAV 1504 may include a payload 1520 in communication with the UAV processor 1516. The payload 1520 may include one or more gas concentration sensors. The payload 1520 may be detachably attached to the UAV 1504. In other embodiments, the payload 1520 may be fixedly attached to the UAV 1504. The payload 1520 may be in communication with the UAV processor 1516. In one embodiment, the payload 1520 may be an ultra-lightweight, low power, Part per Billion (ppb) sensitivity, mid-Infrared ($\lambda$=3-8 µm), open path methane concentration sensor with sampling rate>0.1 Hz. The payload 1520 may record point source gas concentration measurements.

The UAV processor 1516 may also be in communication with an orientation sensor 1528, an inertial measurement unit (IMU) 1530, an altitude sensor 1532, a radar 1534, a LIDAR 1536, and/or a Sonar 1538 for generating additional information on the spatial position of the UAV 1504 during each gas measurement by the payload 1520. The orientation sensor 1528 may be used to determine an orientation of the UAV 1504 relative to ground. The IMU 1530 may be used to determine attitude, velocity and/or position of the UAV 1504. The altitude sensor 1532 may be used to determine an altitude of the UAV 1504. The LIDAR 1536, Sonar 1538, and/or radar 1534 may be used to determine a relative altitude of the UAV 1504.

In some embodiments, the UAV processor 1516 may also be in communication with an anemometer 1542, one or more weather sensors 1544, and/or a barometric pressure sensor 1546. The anemometer 1542 may be used to measure the speed of the wind. The anemometer 1542 may be attached to the UAV 1504 at a point so as to ensure an accurate wind measurement without interfering with the propulsion from the motors 1528 or sensors of the payload 1520. The weather sensor 1544 may measure weather and/or atmospheric conditions. The barometric pressure sensor 1546 may measure a barometric pressure. The anemometer 1542, weather sensor 1544, and/or barometric pressure sensor 1546 may be used to record data at each gas measurement from the payload 1520.

In some embodiments, the UAV processor 1516 may also be in communication with a time measurement device 1540. The time measurement device 1540 may be used to record the time for each gas measurement measured by the payload 1520 of the UAV 1504. Each gas measurement, position measurement, orientation measurement, weather measurement, and/or relative altitude measurement may be 'time-stamped' so as to be combined by the processor 1522 and/or the UAV processor 1516.

The UAV processor 1516 may also be in communication with a transceiver 1548 and/or a wireless radio 1550. The transceiver 1548 and/or wireless radio 1550 may be used to communicate between the UAV 1504 and the processor 1522, the ground control station (GCS) 1526, and/or a cloud server 1524.

The processor 1522, the cloud server 1524, the ground control station (GCS) 1526, and/or the UAV processor 1516 may determine a flight path for the UAV 1504 having the payload 1520. In some embodiments, the flight path may be determined on a site-specific basis. In other embodiments, the flight path may be determined and/or flown via a user of the GCS 1526. In other embodiments, the flight path may be a self-determined, autonomous control. The flight path is used to measure gas concentration along a crosswind transect, and vertical profile, in the vicinity of a possible gas emissions point. This flight plane of the flight path is designed to capture the atmospheric methane background as well as emissions signature, i.e., elevated ambient concentration, from all potential sources at an inspection site.

The UAV 1504 may have the UAV processor 1516 in communication with addressable memory 1518, a GPS 1514, one or more motors 1528, and a power supply 1530. The UAV 1504 may communicate gathered payload 1520 data to the UAV processor 1516. The power supply 1530 may be a battery in some embodiments. In some embodiments, the processor 1522 may be a part of the UAV 1504, the cloud server 1524, the GCS 1526 used to control the UAV 1504, or the like.

The UAV processor 1516 may receive gas data from the one or more gas sensors of the payload 1520. The UAV processor 1516 may also receive spatial position data from the GPS 1514, altitude sensor 1532, location sensor 1518, radar 1534, LIDAR 1536, Sonar 1538, orientation sensor 1528, IMU 1530, and/or onboard avionics 1517. In some embodiments, the UAV processor 1516 may also receive weather data from the weather sensor 1544, the barometric pressure sensor 1546, and/or the anemometer. The UAV processor 1516 may also receive the time from the time measurement device 1540. The UAV processor 1516 may fuse the gas data from the payload 1520 with the UAV 1504 spatial position data, weather data, and/or time to form a UAV Data Packet 1552.

The UAV data packet 1552 may be sent to the processor 1522, ground control station 1526, and/or cloud server 1524 via the transceiver 1548 and/or wireless radio 1550. In some embodiments, the wireless radio 1550 or cellular connection may be used for remote data transfer between the UAV 1504, the GCS 1526, the processor 1522, and/or the cloud server 1524. The wireless interface or cellular connection between the UAV 1504, the GCS 1526, the processor 1522, and/or the cloud server 1524 may be used to performing advanced data analysis functions. Direct, bidirectional data transfer may occur between the UAV 1504 and the GCS 1526, between the UAV 1504 and the cloud server 1524, and/or between the GCS 1524 and the cloud server 1524.

The processor 1522 may be a part of the UAV 1504, the GCS 1526, the cloud server 1524, and/or the weather station 1554 in some embodiments. While multiple sensors and devices are depicted for the UAV 1504, any number of sensors and/or devices may be used based on the system 1500, desired accuracy, time limitations, weight limitations, and the like.

One or more weather stations 1554, 1556, 1558 may provide local weather information to the UAV 1504, payload 1520, GCS 1526, and/or cloud server 1524. The weather stations 1554, 1556, 1558 may also receive information from the UAV 1504, payload 1520, GCS 1526, and/or cloud server 1524.

The first weather station 1554 may include one or more anemometers 1560, one or more pressure sensors 1562, one or more pyranometers 1564, one or more ground temperature sensors 1566, one or more air temperature sensors 1568, one or more atmospheric condition sensors 1570, and one or more location sensors 1572. The anemometer may be used to measure wind speed. The pressure sensor 1562 may measure a pressure. The pyranometer may be used to measure solar irradiance. The ground temperature sensor 1566 may be used to measure a temperature of the ground. The air temperature sensor 1568 may be used to measure a temperature of the air. An atmospheric condition sensor 1570 may be used to measure data relating to the atmosphere. The location sensor 1572 may be used to measure the location of the weather station 1554. Each weather station 1554, 1556, 1558 may include any number of sensors and/or devices based on the system 1500, desired accuracy, number of weather stations over a geographical area, and the like.

In some embodiments, sensors and/or devices of the weather station 1554 may be located and/or duplicated on the UAV 1504. High resolution (<0.1 m/s), high-frequency measurements (>5 Hz) of wind speed and direction may be recorded using one or more wind sensors, and one or more additional weather/micro-meteorological sensors including, air temperature, humidity, atmospheric pressure, solar irradiance, ground surface temperature—from the ground via a weather station 1554, 1556, 1558 and/or from the UAV 1504 as disclosed herein. For example, both the weather station 1554 and the UAV 1504 may include respective anemometers 1560, 1542, which may be used to generate wind speed data. The weather station data may be associated with a time the data was collected and/or generated. The weather station data may be used to generate a Meteorological (MET) data packet 1574. The Meteorological data packet 1574 may be sent to the processor 1522, ground control station 1526, cloud server 1524, and/or UAV 1504. The Meteorological data packet 1574 may include measurements and/or predictions of the atmosphere, weather, temperature, wind patterns, or the like.

Each UAV Data Packet 1552 may be combined with the nearest temporal Meteorological Data Packet 1574 by the processor 1522 and saved on the GCS 1526 and/or cloud server 1524. The data may be uploaded to the cloud server 1524 in real-time, near real-time, or at a later time. The combined UAV data packet 1552 and Meteorological data packet 1574 may be used to determine an elevated ambient emission of the methane source by the processor 1522, GCS 1526, and/or cloud server 1524. The elevated ambient emission may be determined based on a control volume model that combines concentration measurements from the UAV flight plane with measured wind speed, direction and spatial gradient to determine the mass flow rate emissions from sources in the inspection area.

This determined elevated ambient emission may used to generate a back trajectory, store the back trajectories in a grid, determine a gas source location probability, and/or generate an overlay of the probability of the gas source location by the processor 1522, GCS 1526, and/or cloud server 1524. The display 1576 may show the overlay on a map, satellite image, aerial image, two-dimensional color map, two-dimensional contour map, and/or three-dimensional topographical surface/mesh.

Figure 16:
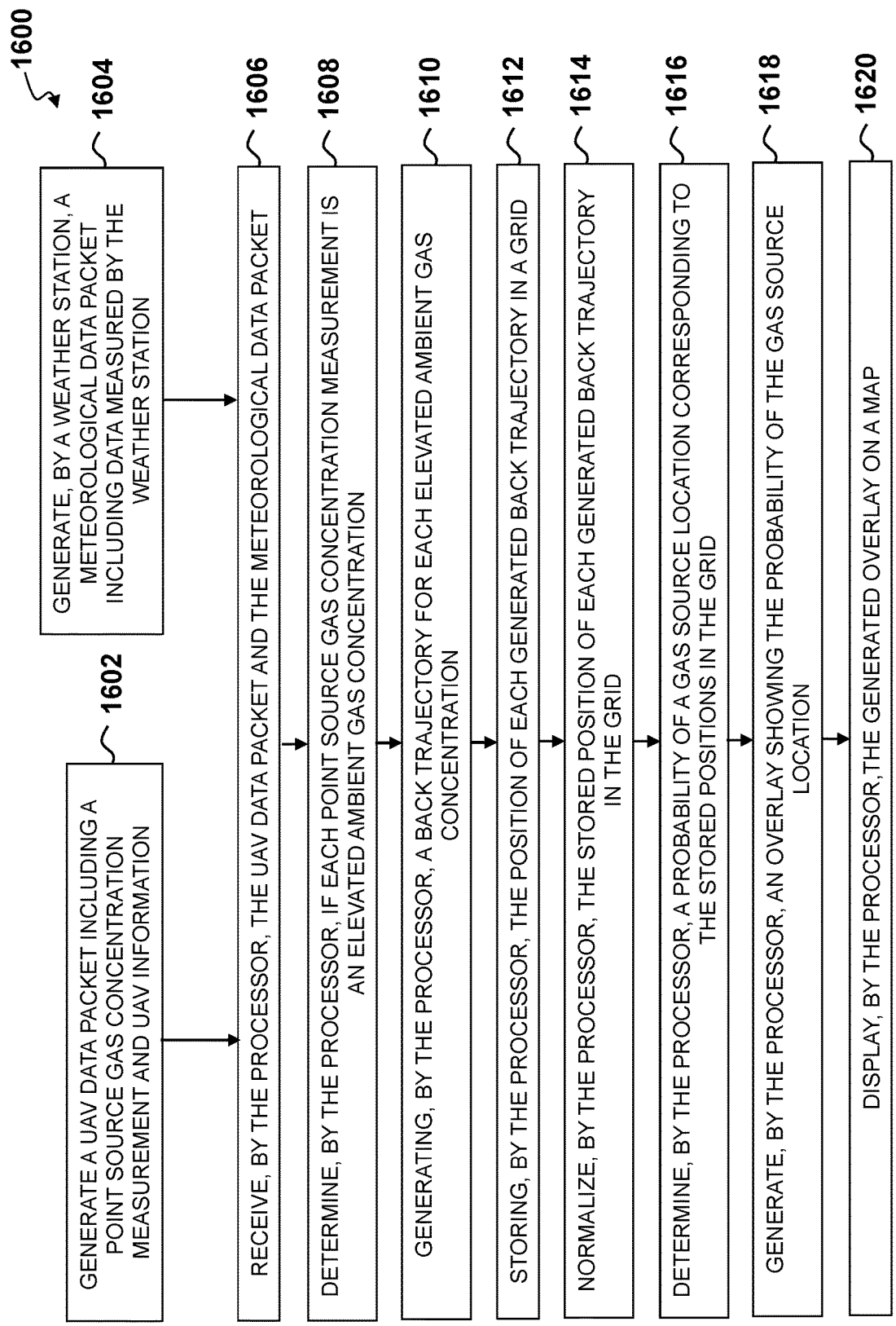
FIG. 16 depicts a high-level flowchart of a method embodiment of detecting and localizing methane sources via point source gas measurements, according to one embodiment.

FIG. 16 depicts a high-level flowchart of a method 1600 embodiment of detecting and localizing methane sources via point source gas measurements, according to one embodiment. The method 1600 may include generating a UAV data packet including a point source gas concentration measurement and UAV information (step 1602). The UAV data packet may be generated by one or more UAVs. The method 1600 may also include generating, by a weather station, a Meteorological data packet including data measured by the weather station. One or more weather stations may be used. The weather station may be located on the UAV or another UAV in some embodiments. The weather station may include third-party data in some embodiments. The method 1600 then includes receiving, by the processor, the UAV data packet and the Meteorological data packet (step 1606). The UAV data packet may be joined with the nearest temporal Meteorological data packet.

The method 1600 may then include determining if each point source gas concentration measurement is an elevated ambient gas concentration (step 1608). Levels of methane, or other gasses, may be present in the atmosphere at certain levels. The processor determines if an elevated level of methane, or another gas, is detected which could indicate a gas leak from a gas source. The method 1600 may then include generating a back trajectory for each elevated ambient gas concentration (step 1610). The point source gas concentration reading location, and meteorological data allow the system and method 1600 to use a stochastic particle back trajectory model to determine a back trajectory of each elevated ambient gas concentration. The back trajectory model allows the system and method 1600 to determine a probable location of a gas source by combining the cumulative calculated back trajectories.

The method 1600 may then include storing the position of each generated back trajectory in a grid (step 1612). In some embodiments, the grid may be two-dimensional (2D) having x, y coordinates for each cell in the grid. In other embodiments, the grid may be three-dimensional (3D) having x, y, z coordinates for each cell in the grid. Each cell in the grid may be summed to find a density of each cell in the grid. The method 1600 may then include normalizing the stored position of each generated back trajectory in the grid (step 1614). Normalizing may be used to clean up the results of the system and method 1600. For example, an entire area may have a non-zero probability of containing a gas source causing the detected elevated ambient gas concentration. By normalizing the results, the probability may be confined to an area with a higher likelihood of containing the gas source.

The method 1600 may then include determining a probability of a gas source location corresponding to the stored positions in the grid (step 1616). The method 1600 may then include generating an overlay showing the probability of the gas source location (step 1618). The method 1600 may then include displaying the generated overlay on a map (step 1612). The map may be 2D map or a 3D map. The displayed overlay and map may be used to identify the most likely sources of gas leaks, which may then be used to take corrective action to repair equipment, minimize or eliminate gas leaks, or the like. The processor having addressable memory may be a part of a ground control system (GCS), a cloud server, a remote server, and/or one or more UAVs.

Figure 17:
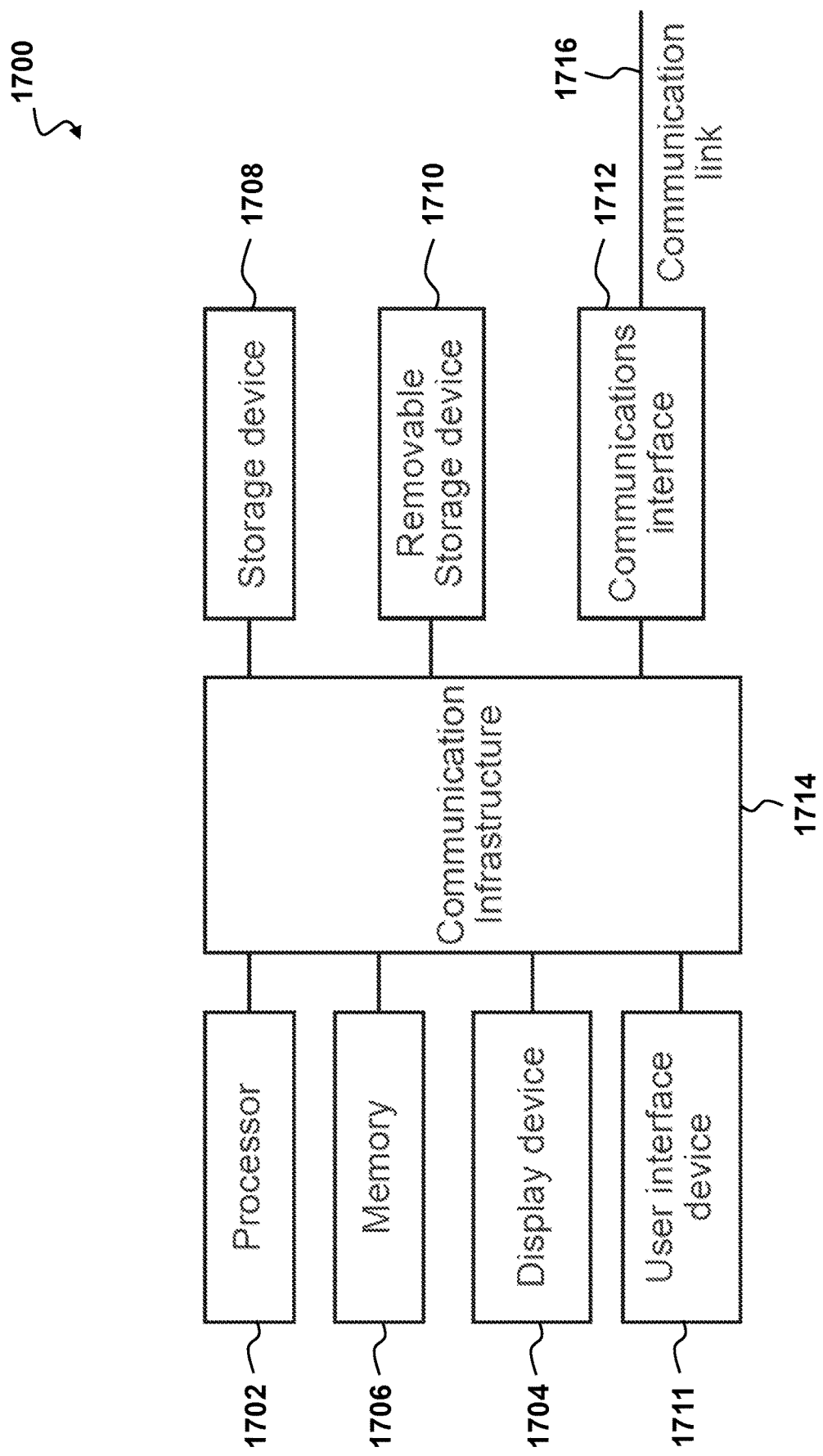
FIG. 17 shows a high-level block diagram and process of a computing system for implementing an embodiment of the system and process.

FIG. 17 is a high-level block diagram 1700 showing a computing system comprising a computer system useful for implementing an embodiment of the system and process, disclosed herein. Embodiments of the system may be implemented in different computing environments. The computer system includes one or more processors 1702, and can further include an electronic display device 1704 (e.g., for displaying graphics, text, and other data), a main memory 1706 (e.g., random access memory (RAM)), storage device 1708, a removable storage device 1710 (e.g., removable storage drive, a removable memory module, a magnetic tape drive, an optical disk drive, a computer readable medium having stored therein computer software and/or data), user interface device 1711 (e.g., keyboard, touch screen, keypad, pointing device), and a communication interface 1712 (e.g., modem, a network interface (such as an Ethernet card), a communications port, or a PCMCIA slot and card). The communication interface 1712 allows software and data to be transferred between the computer system and external devices. The system further includes a communications infrastructure 1714 (e.g., a communications bus, cross-over bar, or network) to which the aforementioned devices/modules are connected as shown.

Information transferred via communications interface 1714 may be in the form of signals such as electronic, electromagnetic, optical, or other signals capable of being received by communications interface 1714, via a communication link 1716 that carries signals and may be implemented using wire or cable, fiber optics, a phone line, a cellular/mobile phone link, an radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 1712. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 18:
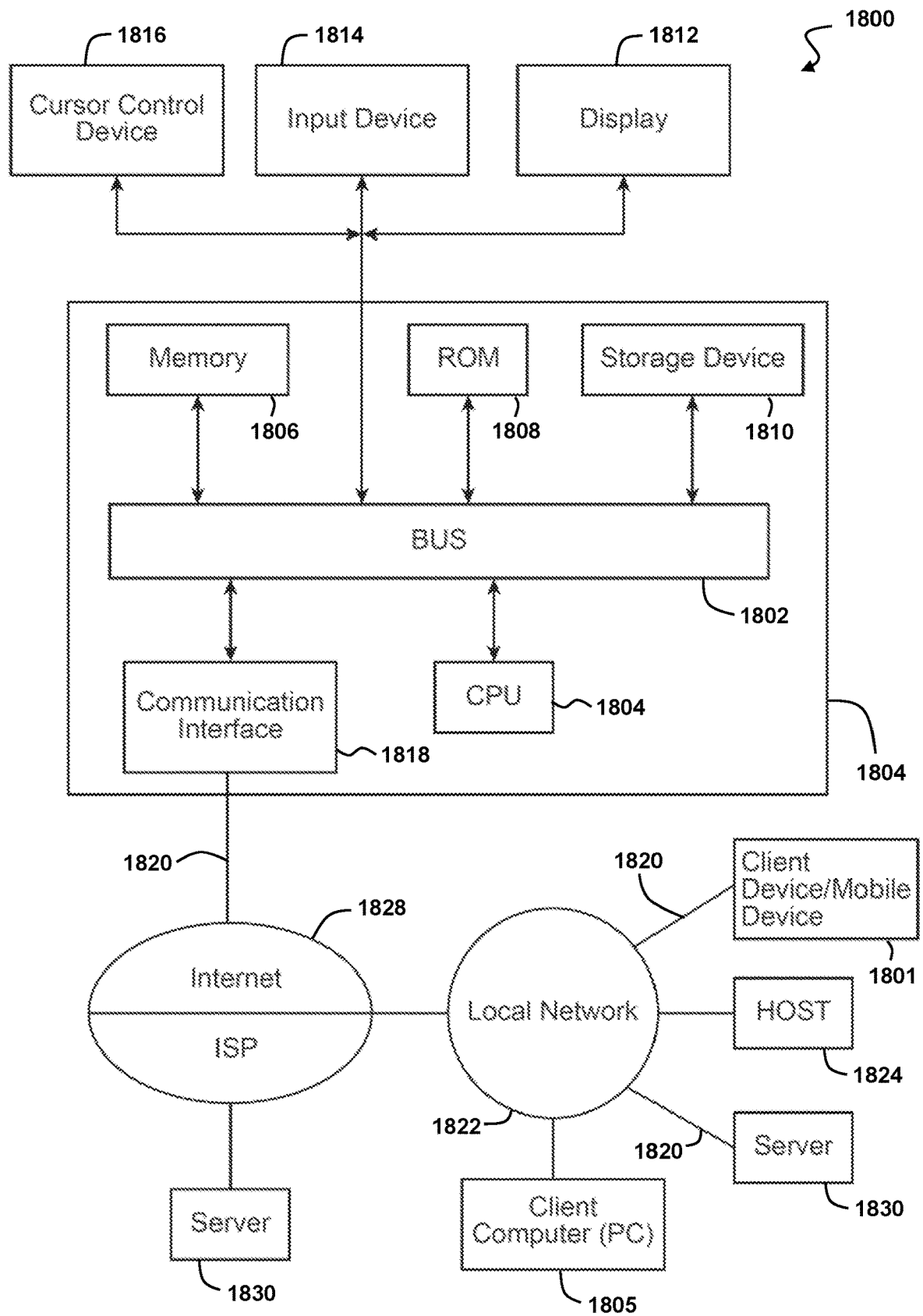
FIG. 18 shows a block diagram and process of an exemplary system in which an embodiment may be implemented.

FIG. 18 shows a block diagram of an example system 1800 in which an embodiment may be implemented. The system 1800 includes one or more client devices 1801 such as consumer electronics devices, connected to one or more server computing systems 1830. A server 1830 includes a bus 1802 or other communication mechanism for communicating information, and a processor (CPU) 1804 coupled with the bus 1802 for processing information. The server 1830 also includes a main memory 1806, such as a random access memory (RAM) or other dynamic storage device, coupled to the bus 1802 for storing information and instructions to be executed by the processor 1804. The main memory 1806 also may be used for storing temporary variables or other intermediate information during execution or instructions to be executed by the processor 1804. The server computer system 1830 further includes a read only memory (ROM) 1808 or other static storage device coupled to the bus 1802 for storing static information and instructions for the processor 1804. A storage device 1810, such as a magnetic disk or optical disk, is provided and coupled to the bus 1802 for storing information and instructions. The bus 1802 may contain, for example, thirty-two address lines for addressing video memory or main memory 1806. The bus 1802 can also include, for example, a 32-bit data bus for transferring data between and among the components, such as the CPU 1804, the main memory 1806, video memory and the storage 1810. Alternatively, multiplex data/address lines may be used instead of separate data and address lines.

The server 1830 may be coupled via the bus 1802 to a display 1812 for displaying information to a computer user. An input device 1814, including alphanumeric and other keys, is coupled to the bus 1802 for communicating information and command selections to the processor 1804. Another type or user input device comprises cursor control 1816, such as a mouse, a trackball, or cursor direction keys for communicating direction information and command selections to the processor 1804 and for controlling cursor movement on the display 1812.

According to one embodiment, the functions are performed by the processor 1804 executing one or more sequences of one or more instructions contained in the main memory 1806. Such instructions may be read into the main memory 1806 from another computer-readable medium, such as the storage device 1810. Execution of the sequences of instructions contained in the main memory 1806 causes the processor 1804 to perform the process steps described herein. One or more processors in a multi-processing arrangement may also be employed to execute the sequences of instructions contained in the main memory 1806. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 1804 for execution. Such a medium may take many forms, including but not limited to, non-volatile media, volatile media, and transmission media. Non-volatile media includes, for example, optical or magnetic disks, such as the storage device 1810. Volatile media includes dynamic memory, such as the main memory 1806. Transmission media includes coaxial cables, copper wire and fiber optics, including the wires that comprise the bus

1802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 1804 for execution. For example, the instructions may initially be carried on a magnetic disk of a remote computer. The remote computer can load the instructions into its dynamic memory and send the instructions over a telephone line using a modem. A modem local to the server 1830 can receive the data on the telephone line and use an infrared transmitter to convert the data to an infrared signal. An infrared detector coupled to the bus 1802 can receive the data carried in the infrared signal and place the data on the bus 1802. The bus 1802 carries the data to the main memory 1806, from which the processor 1804 retrieves and executes the instructions. The instructions received from the main memory 1806 may optionally be stored on the storage device 1810 either before or after execution by the processor 1804.

The server 1830 also includes a communication interface 1818 coupled to the bus 1802. The communication interface 1818 provides a two-way data communication coupling to a network link 1820 that is connected to the world wide packet data communication network now commonly referred to as the Internet 1828. The Internet 1828 uses electrical, electromagnetic or optical signals that carry digital data streams. The signals through the various networks and the signals on the network link 1820 and through the communication interface 1818, which carry the digital data to and from the server 1830, are exemplary forms or carrier waves transporting the information.

In another embodiment of the server 1830, interface 1818 is connected to a network 1822 via a communication link 1820. For example, the communication interface 1818 may be an integrated services digital network (ISDN) card or a modem to provide a data communication connection to a corresponding type of telephone line, which can comprise part of the network link 1820. As another example, the communication interface 1818 may be a local area network (LAN) card to provide a data communication connection to a compatible LAN. Wireless links may also be implemented. In any such implementation, the communication interface 1818 sends and receives electrical electromagnetic or optical signals that carry digital data streams representing various types of information.

The network link 1820 typically provides data communication through one or more networks to other data devices. For example, the network link 1820 may provide a connection through the local network 1822 to a host computer 1824 or to data equipment operated by an Internet Service Provider (ISP). The ISP in turn provides data communication services through the Internet 1828. The local network 1822 and the Internet 1828 both use electrical, electromagnetic or optical signals that carry digital data streams. The signals through the various networks and the signals on the network link 1820 and through the communication interface 1818, which carry the digital data to and from the server 1830, are exemplary forms or carrier waves transporting the information.

The server 1830 can send/receive messages and data, including e-mail, program code, through the network, the network link 1820 and the communication interface 1818. Further, the communication interface 1818 can comprise a USB/Tuner and the network link 1820 may be an antenna or cable for connecting the server 1830 to a cable provider, satellite provider or other terrestrial transmission system for receiving messages, data and program code from another source.

The example versions of the embodiments described herein may be implemented as logical operations in a distributed processing system such as the system 1800 including the servers 1830. The logical operations of the embodiments may be implemented as a sequence of steps executing in the server 1830, and as interconnected machine modules within the system 1800. The implementation is a matter of choice and can depend on performance of the system 1800 implementing the embodiments. As such, the logical operations constituting said example versions of the embodiments are referred to for e.g., as operations, steps or modules.

Similar to a server 1830 described above, a client device 1801 can include a processor, memory, storage device, display, input device and communication interface (e.g., e-mail interface) for connecting the client device to the Internet 1828, the ISP, or LAN 1822, for communication with the servers 1830.

The system 1800 can further include computers (e.g., personal computers, computing nodes) 1805 operating in the same manner as client devices 1801, wherein a user can utilize one or more computers 1805 to manage data in the server 1830.

Figure 19:
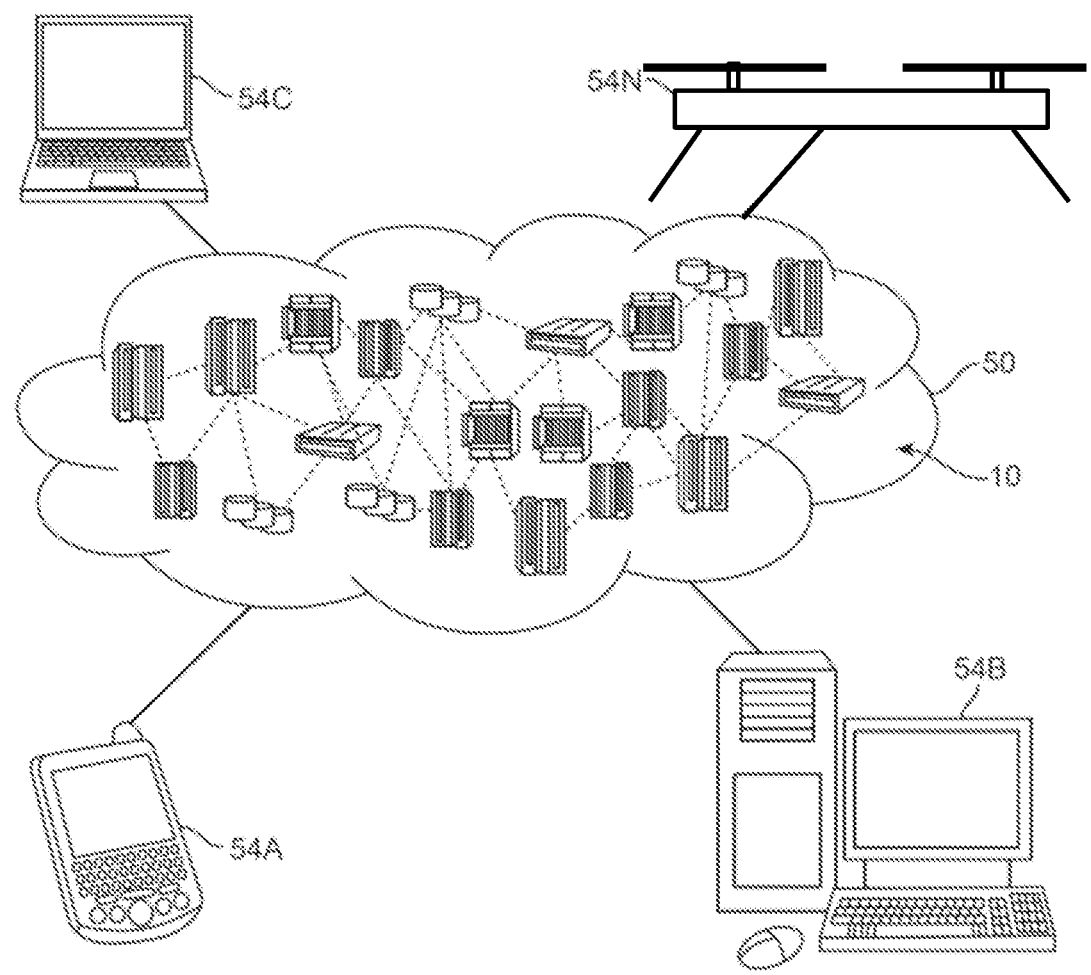
FIG. 19 depicts a cloud-computing environment for implementing an embodiment of the system and process disclosed herein.

Referring now to FIG. 19, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 19 are intended to be illustrative only and that computing nodes 10 and cloud computing environment 50 can communicate with any type of computerized device over any type of network and/or network addressable connection (e.g., using a web browser).

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention herein disclosed by way of examples should not be limited by the particular disclosed embodiments described above.

What is claimed is:

1. A method, comprising:
generating, by one or more in situ trace-gas concentration sensors disposed on a vehicle, a plurality of in situ point source trace-gas concentration measurements at a plurality of spatial positions, the one or more in situ trace-gas concentration sensors measuring trace-gas in situ;
generating, by the vehicle, spatial position data corresponding to the plurality of spatial positions;
generating, by a weather station, a meteorological data containing wind vector;
receiving, by a ground control station (GCS) having a processor with addressable memory, the plurality of in situ point source trace-gas concentration measurements;
receiving, by the GCS, the spatial position data of any one of the vehicle or the one or more in situ trace-gas concentration sensors corresponding to the received in situ point source trace-gas concentration measurements;
receiving, by the GCS, the meteorological data corresponding to each in situ point source concentration trace-gas measurement;
determining, by the GCS, if each in situ point source trace-gas concentration measurement is an elevated ambient trace-gas concentration;
generating, by the GCS, a back trajectory for each elevated ambient trace-gas concentration based on the spatial position where the elevated ambient trace-gas concentration occurs and the meteorological data corresponding to the spatial position where the elevated ambient trace-gas concentration occurs;
storing, by the GCS, the position of each generated back trajectory in a grid;
summing, by the GCS, the stored positions of the generated back trajectories within each cell of the grid;
determining, by the GCS, a probability of a trace-gas source location corresponding to the summed stored positions in the grid; and
displaying, on a display in communication with the GCS, an overlay showing the probability of the trace-gas source location.

2. The method of claim 1, wherein the vehicle is one or more unmanned aerial vehicles (UAVs), and the one or more trace-gas concentration sensors are disposed on one or more unmanned aerial vehicles (UAVs).

3. The method of claim 2, wherein receiving the spatial position data further comprises:
receiving, by the GCS, the spatial position data of the UAVs corresponding to the received in situ point source trace-gas source concentration measurements.

4. The method of claim 1, wherein the meteorological data comprises an instantaneous wind vector, an average wind vector, a wind vector component magnitude variance, and a wind vector component direction variance.

5. The method of claim 1 wherein the in situ point source trace-gas concentration measurement is a methane gas measurement.

6. The method of claim 1 wherein the generated back trajectory is generated using a stochastic particle trajectory model.

7. The method of claim 1, wherein storing the position of each generated back trajectory in a grid further comprises:
summing, by the GCS, the stored position within each cell of the grid.

8. The method of claim 1 further comprising:
normalizing, by the GCS, the stored position of each generated back trajectory in the grid.

9. The method of claim 8 further comprising:
determining, by the GCS, a perimeter of the trace-gas source location based on the normalized stored position of each generated back trajectory.

10. The method of claim 1, wherein displaying the overlay is performed on a two-dimensional (2D) map.

11. The method of claim 1, wherein displaying the overlay is performed on a three-dimensional (3D) map.

12. The method of claim 1, wherein the grid is a two-dimensional (2D) grid.

13. The method of claim 1, wherein the grid is a three-dimensional (3D) grid.

14. The method of claim 1, before the step of determining an elevated ambient trace-gas concentration, further comprising:
calculating, by the GCS, a background trace-gas concentration to determine if each in situ point source trace-gas concentration measurement is an elevated ambient trace-gas concentration, the step of calculating a background trace-gas concentration including:
selecting data of the plurality of in situ point source trace-gas concentration measurements for a time period;
converting a spatial coordinate frame to along a path distance of the selected data of the plurality of in situ point source trace-gas concentration measurements;
filtering the selected data of the plurality of in situ point source trace-gas concentration measurements as a function of spatial coordinate using a filter to obtain the background trace-gas concentration.

15. The method of claim 14, wherein the filter is a sliding window median filter.

16. The method of claim 14, wherein the filter is a statistical filter.

17. The method of claim 14, wherein the step of determining an elevated ambient trace-gas concentration includes:
subtracting the background trace-gas concentration from each of the plurality of in situ point source trace-gas concentration measurements to obtain a concentration enhancement; and
applying a statistical filter to the concentration enhancement to identify spikes.

18. The method of claim 1, wherein the step of determining an elevated ambient trace-gas concentration includes:
subtracting the background trace-gas concentration from each of the plurality of in situ point source trace-gas concentration measurements to obtain a concentration enhancement; and
applying a statistical filter to the concentration enhancement to identify spikes.

19. A system comprising:
a vehicle configured to move through a plurality of spatial positions and generate spatial position data corresponding to the plurality of spatial positions;
one or more in situ trace-gas concentration sensors disposed on the vehicle and configured to generate a plurality of in situ point source trace-gas concentration measurements at the plurality of spatial positions, the one or more in situ trace-gas concentration sensors measuring trace-gas in situ;
a weather station generating a meteorological data containing wind vector;

a ground control station (GCS) having a processor with addressable memory, the processor configured to:
- receive the plurality of in situ point source trace-gas concentration measurements;
- receive the spatial position data of any one of the vehicle or the one or more in situ trace-gas concentration sensors and corresponding to the received in situ point source trace-gas concentration measurements;
- receive the meteorological data corresponding to each in situ point source concentration trace-gas measurement;
- determine if each in situ point source trace-gas concentration measurement is an elevated ambient trace-gas concentration;
- generate a back trajectory for each elevated ambient trace-gas concentration based on the spatial position where the elevated ambient trace-gas concentration occurs and the meteorological data corresponding to the spatial position where the elevated ambient trace-gas concentration measurement occurs;
- store the position of each generated back trajectory in a grid;
- sum the stored positions of the generated back trajectories within each cell of the grid; and
- determine a probability of a trace-gas source location corresponding to the summed stored positions in the grid;

a display configured to communicate with the GCS and generate an overlay showing the probability of the trace-gas source location.

20. The system of claim 19, further comprising:
one or more unmanned aerial vehicles (UAVs), wherein the one or more in situ trace-gas concentration sensors are disposed on the one or more UAVs.

* * * * *